United States Patent
Wendt

(10) Patent No.: US 7,378,954 B2
(45) Date of Patent: May 27, 2008

(54) SAFETY INDICATOR AND METHOD

(76) Inventor: Barry Myron Wendt, 9625 W. Russell Rd., Apt. 2072, Las Vegas, NV (US) 89148

( * ) Notice: Subject to any disclaimer, the term of this patent is extended or adjusted under 35 U.S.C. 154(b) by 161 days.

(21) Appl. No.: 11/255,609

(22) Filed: Oct. 21, 2005

(65) Prior Publication Data

US 2007/0241261 A1  Oct. 18, 2007

(51) Int. Cl.
*G08B 5/22* (2006.01)
*G01J 1/02* (2006.01)
*G01T 1/02* (2006.01)
*H04Q 1/00* (2006.01)

(52) U.S. Cl. .............................. 340/539.11; 340/539.12; 340/539.13; 340/539.17; 340/539.19; 340/539.27; 340/539.29; 250/370.07

(58) Field of Classification Search ................ 250/584, 250/370.07; 340/521, 539.1, 539.11, 539.12, 340/539.13, 539.16, 539.17, 539.19, 539.26, 340/539.27, 539.29
See application file for complete search history.

(56) References Cited

U.S. PATENT DOCUMENTS

| | | | | |
|---|---|---|---|---|
| 4,460,830 A | * | 7/1984 | Allemand et al. | 250/370.07 |
| 4,672,309 A | * | 6/1987 | Gandhi | 324/95 |
| 4,813,789 A | * | 3/1989 | Olsen | 374/32 |
| 4,884,132 A | * | 11/1989 | Morris et al. | 358/479 |
| 5,256,960 A | * | 10/1993 | Novini | 324/72 |
| 5,604,483 A | * | 2/1997 | Giangardella et al. | 340/565 |
| 5,742,233 A | * | 4/1998 | Hoffman et al. | 340/573.1 |
| 6,239,700 B1 | * | 5/2001 | Hoffman et al. | 340/539.13 |
| 6,624,754 B1 | * | 9/2003 | Hoffman et al. | 340/573.1 |
| 7,038,590 B2 | * | 5/2006 | Hoffman et al. | 340/573.1 |
| 2003/0234725 A1 | | 12/2003 | Lemelson et al. | |

* cited by examiner

*Primary Examiner*—John R. Lee
(74) *Attorney, Agent, or Firm*—Aaron Passman

(57) ABSTRACT

A safety indicator monitors environment conditions detrimental to humans e.g., hazardous gases, air pollutants, low oxygen, radiation levels of EMF or RF and microwave, temperature, humidity and air pressure retaining a three month history to upload to a PC via infra red data interface or phone link. Contaminants are analyzed and compared to stored profiles to determine its classification and notify user of an adversity by stored voice messages from, via alarm tones and associated flashing LED, via vibrator for silent operation or via LCD. Environmental radiation sources are monitored and auto-scaled. Instantaneous radiation exposure level and exposure duration data are stored for later readout as a detector and dosimeter. Scans for EMF allow detection with auto scaling of radiation levels and exposure durations are stored for subsequent readout. Electronic bugs can be found with a high sensitivity EMF range setting. Ambient temperature measurements or humidity and barometric pressure can be made over time to predict weather changes. A PCS RF link provides wireless remote communications in a first responder military use by upload of alarm conditions, field measurements and with download of command instructions. The link supports reception of telemetry data for real time remote monitoring of personnel via the wrist band for blood pressure, temperature, pulse rate and blood oxygen levels are transmitted. Commercial uses include remote environmental data collection and employee assignment tasking. GPS locates personnel and reporting coordinates associated with alarm occurrences and associated environmental measurements.

76 Claims, 14 Drawing Sheets

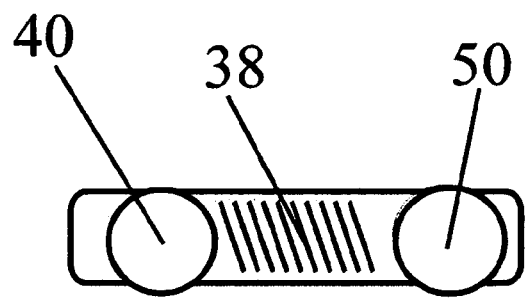
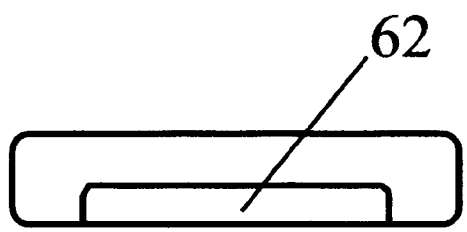
Figure-4
Figure-5
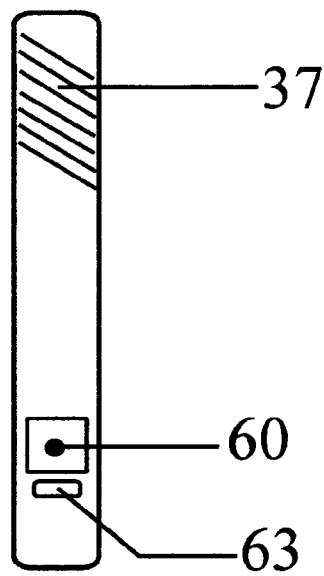
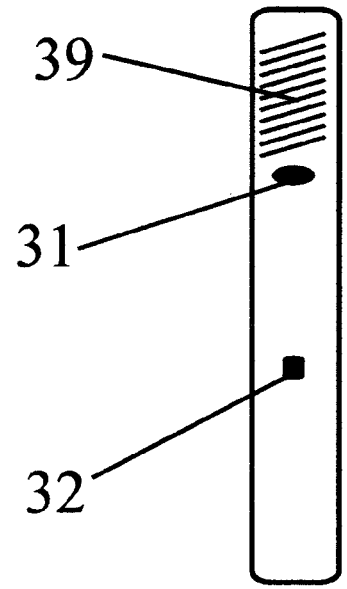
Figure-2
Figure-3

SAFETY INDICATOR AND METHOD

CROSS-REFERENCE TO RELATED APPLICATIONS

Design patent application filed same date is entitled Personal Safety Indicator, Docket BMW 2

STATEMENT REGARDING FEDERALLY SPONSORED RESEARCH

Sequence listing not applicable

BACKGROUND OF THE INVENTION

This is most like United States Patent application disclosure #20030234725 of an intelligent alarm system for detecting hazardous situations in a building, informing building occupants of optimal escape routes or survival strategies and assisting emergency personnel in rescuing people inside the building. Building hazards, including fire, earthquakes, intruders, etc., have the potential for large numbers of casualties. Effective building alarm systems must have the capability to process a plurality of input sensor types to determine the nature of the situation involving danger to persons in the building. The building alarm system must also have more than simple audio/visual outputs for helping people in the building find safe escape routes.

Detection and warning of hazards that may exist in a surrounding environment is crucial to the safety of each individual. Sensor technology allows for the monitoring of many parameters including, but not limited to, carbon monoxide (CO), hydrocarbons, temperature, vibration, etc. Portable personal sensor devices designed to protect the individual are not common or reasonably affordable. Sophisticated sensor technology can minimize exposure to hazardous or unsafe conditions or environs.

Many dangers to which a human might be exposed and be unaware are not apparent until it is too late. Such unappreciated hazards can result is immediate injuries minor or sever. In the complex modern world man made and natural perils can without warning be unrecognized and injury will result. Dangers of terrorism, climatic conditions, industrial mishaps and misuse of products or improperly made equipment can lead to exposures that should be avoided to preserve one health and well being. The possibilities for hazards, and dealing with them, must be determined, analyzed recorded in order to adequately alert persons within the environs of dangerous situations. A portable personal safety system designed to use of stored parameters based on the knowledge and resources of experienced technical experts in diverse fields relating to emergency situations including, but not limited to, fire fighting, toxic fume detection, earthquake physics, human tolerance to radiation, gases, temperature and medical problems detectable from changes in surrounding conditions and/or monitored bodily physiology will aid in protecting the individual.

Now, most individuals are limited to their own senses; that is environmental ambiance which they can perceive. Often hazards unsusceptible to recognition by the human senses cause damage over a long period of exposure. In the 1940's before radiation badges appeared it was thought odd that the danger could not be perceived until the individual was harmed. Today man made environmental dangers, hazards and conditions are appreciated and understood but not monitored and recorded over time. Even noise levels are recognized by OSHA and legislation exists to control and limit human exposure but recreation activities result in injuries, e.g., hearing is still damaged at rock concerts, during hunting, around auto races, etc. No portable personal safety monitor is available or known to check, record and warn of any potential for harm. We now can measure hazards, are aware of dangers and understand the risks of our civilization and know the need to protect against them but a device to advise each individual of a need to safeguard oneself has not been available. Terrorism and catastrophic weather conditions add new needs for a portable personal safety monitor and most certainly the measurement of dangers associated with those current dangers can to some extent be followed.

Communication during situations of calamity via existing land based networks has failed when natural and man induced disasters happen so a portable personal safety monitor that affords two way communication not subject to local infrastructure is essential for the safety and well being of the individual. Even cell phone technology has been shown to have its limitations when a catastrophe occurs. Transcending such limited communication systems with a portable personal safety monitor is needed. Moreover the ability to monitor vital signs of the individual and transmit them to a central station for monitoring recording exposure levels and stress received by the individuals is important to protecting the well being. While location determination is of value to the employer of the individual, the concept without including protecting the individual's safety is less than ideal and not particularly useful. The need exist to monitor vital signs and location so that informed decisions about directing the endangered party from the hazard can be made.

SUMMARY OF THE INVENTION

A portable personal safety indicator monitors environment conditions that are detrimental to human health. The portable personal safety indicator continuously monitors the environment for at least hazardous gases, elevated levels of other air pollutants including smoke and exhaust fumes, low oxygen levels, ionizing radiation levels, adverse radiation levels of Electro Magnetic Radiation "EMF" radiation including RF and microwave transmissions, unsafe temperature, humidity and air pressure. The Portable personal safety indicator maintains a three month user history of all exposure levels and duration for upload to a PC via infra red data interface for reporting functions. A field of use is mobile monitoring for personal safety in environments with dangerous air born gases and other air pollutants warning the user when a level of air born contamination is present which may represent a health threat. Air contaminants are analyzed and compared to stored profiles to determine what family classification of contaminant is present when assessing a threat. Detection and classification of several hundred different toxic gases is possible. The portable personal safety indicator notifies the user of an adverse environment by stored voice messages in an embedded audio circuit with speaker or headphones, via alarm tones and associated flashing LED, via vibrator that may be embedded for silent operation or via the alphanumeric LCD display. If headphones are plugged in, the internal speaker circuit is bypassed. When the user selects audio or silent operation for alerts, flashing LEDS with detail information located on the backlit LCD display is also available.

The portable personal safety indicator continuously monitors the environment for nominal oxygen levels as determined by factory default settings and provides alerts if low oxygen levels are detected. The user may also set a desired range of acceptable oxygen levels so an alarm is generated measures and signals if the measured level is outside of the user specified range. Environmental radiation sources are monitored and if radiation is detected, the portable personal safety indicator alerts and auto-scales to measure the radiation level.

AGC (analog gain controlled) used in amplifiers is a well known electronic design concept commonly used in RF receivers. Typical AGC circuits are designed to control the overall gain of an analog circuit to eliminate saturation of the final amplifier stage which would result in the loss or distortion of received information. Instrumentation used in detecting radiation and EMF energy usually consists of a manual form of analog gain control implemented through the setting of control knobs and switches. This is partially due to the sensitivity required at low signal levels requiring the isolation of circuits to maintain a very low noise floor. The large signal bandwidth requirement of the portable personal safety indicator necessitated a special form of AGC such that it could automatically track the smallest detectable signal without saturation or distortion of the end stage amplifier if a sudden surge in received signal was experienced. There is an essential need in dosimeter applications where accurately measured and stored EMF or radiation exposure levels and durations are accumulated.

Essentially, the portable personal safety indicator uses a new auto-scaling analog gain concept that forces the output of the receive circuits to hover at a center range of its current gain/output setting. This results in the best accuracy without loss of information as the receiver at any point in time has the most dynamic range to readjust to a decaying or increasing signal prior to establishment of a new scaling factor. If one assumes the output could range from 0-10 volts, than for any given input signal the gain of the circuit is adjusted so the average output is 5 volts. The resulting measurement consists of a value (0-10) and an amplification scaling factor which could be from 0.00001 to 10,000. Given the preceding an output value of 7 with a gain setting of 0.001 results in a measurement value of 7,000 which is equal to the value divided by the scaling factor. Specifically, an output value of 5 with a gain setting of 1000 results in an actual measurement of 5/1000 which equals 0.005. The auto-scaling algorithm monitors sensor circuit outputs and adjusts the analog gain of the receiver circuits so clipping does not occur based a moving average of the received signal. As the signal average moves towards ground the gain is increased, as the average moves towards VCC, the gain is reduced such that a midrange average output is maintained between ground and VCC. VCC is a positive supply voltage which could be anything such as 3.6 volts, 5 volts, etc. Instantaneous radiation exposure level and exposure duration data are stored for later readout.

The portable personal safety indicator functions as a radiation detector and dosimeter. Measurements from 0 to 3,000,000 CPM, 0.5 to 3000 mR/hr with an accuracy of +/−10% are possible. User defined set points, set trigger detection alarms thresholds. The portable personal safety indicator functions as an EMF detector and EMF dosimeter. Continuous scans for EMF, in the frequency range of approximately 100 khz to 20 ghz allows detecting from 1 nano waft to 10 watts RMS/cm$^2$ with an accuracy of +/−10%. EMF detection includes an auto scaling circuit to accurately detect EMF radiation levels and exposure durations that are stored for subsequent readout. Factory default alarm set points can be reconfigured depending on user application. Electronic bugs can be found with a high sensitivity EMF range setting. Ambient temperature measurements from −55 to +125 degrees centigrade accurate to +/−0.5 degrees centigrade or, humidity from 0% to 100% with an accuracy of +/−1% relative humidity and barometric pressure from 750 to 1100 mille-bar (mbar), with +/−0.5 mbar accuracy can be made.

Measurements of temperature, humidity, EMF (lightning) and pressure over time can with software predict subtle or potentially dangerous weather changes functioning as a portable weather station. Ambient data of oxygen, temperature, humidity and pressure are used to normalize gas sensor readings as environmental variables can affect typical gas sensor readings by more than 400%. Due to the incorporation and real-time measurement of these environmental conditions, the portable personal safety indicator is the first accurate self calibrating portable gas sensor available. A PCS RF link provides wireless remote communications via PCS cell phone technology in for example first responder command control applications to upload of alarm conditions, field measurements and with download of command instructions to field personnel. Military applications including troop monitoring, deployment and command control are supported.

Common commercial uses include remote environmental data collection and employee assignment tasking. The PCS RF link also supports reception of telemetry data for real time remote monitoring of personnel via the optional wrist band bio-monitoring which periodically samples of wearer's data including blood pressure, temperature, pulse rate and blood oxygen levels and transmits this data to the portable personal safety indicator. Field personnel are critically monitored as support for first responder and military or for remote medical patient care. The portable personal safety indicator environmental measurements with the wrist band bio-monitor provide for a cause/effect reporting capability. The portable personal safety indicator includes a GPS option useful for remotely locating personnel and reporting coordinates associated with alarm occurrences and associated environmental measurements. Infra red data interface provides for uploading and downloading data at rates up to 250 k baud to a PC via an optional docking station which also provides for recharging the battery pack. Infra red data interface also allows for exchange of data with the portable personal safety indicator. Uploaded data can be formatted for custom reporting requirements to support a wide range of applications using available proprietary reporting software. Up to three months of sensor data is stored for later custom reports. Battery pack with a typical continuous use lasts thirty two hours per charge and can be recharged in 1.2 hours with an expected life cycle of 500 charges (approximately 3 years of use) before battery pack 66 replacement is required. The portable personal safety indicator incorporates a high quality microphone and digital audio storage to enable digital recording of up to 3 hours of audio stored for subsequent playback or uploading and downloading via the PCS RF link 131 or infra red data interface 160. Recording and playback sample rates of up to 44 kHz with 8, 10 or 12 bit A/D, D/A resolution are available for playback. Digital recorder functions and play selections include music. If an alarm is given, the user has the portable personal safety indicator to determine what the potential environmental threat is and to determine when they have removed themselves from the threat environment.

The portable personal safety indicator is a lightweight device with an approximate size of 2-¼ inches wide by 3-½ inches high by 1 inch thick with weight and construction characteristics similar to cell phones. The portable personal safety indicator may be worn externally by a clip to attach to a belt, pocket, shirt or lapel; holster mounts for attachment to a vehicle dash or by plugging into an AC outlet are possible in addition to portable or hand held use. The portable personal safety indicator is enclosed in a plastic clam shell type case that is secured by screws. The internal assembly consists of several circuit boards layered in a stack configuration with header interconnects between layers. For compactness the circuit board construction is predominately type-2 surface mount technology (i.e.; components mounted on both sides of the circuit boards). The combination of type-2 construction, layered boards and miniature surface mount components allow for a large number of product functions to be incorporated in a small footprint, lightweight package. The preferred embodiment consists of a charcoal gray plastic case with silkscreen legends in black with neon blue borders. Variations in the physical characteristics of the portable personal safety indicator, including methods of construction, material used or nomenclature should be considered as evident alternatives to the current description or implementation.

Portable personal safety indicator is a comprehensive environmental monitoring device suitable for mobile personal safety use in these circumstances: automatically monitor the environment for dangerous air born gases and other air pollutants, detect and classify up to several hundred different toxic gases, notify the user of environmental problems, continuously monitor the environment for ambient oxygen levels, monitors the environment for radiation sources, provides an indication of radiation detection and radiation dosage, continuously scan for electro magnetic radiation, EMF radiation detector and EMF dosimeter, locate electronic bugs including RF transmitters, microphones and cameras, monitor and measure ambient temperature, humidity, barometric pressure, predict weather changes and function as a portable weather station.

Portable personal safety indicator is the first accurate self calibrating portable gas sensor or EMF dosimeter available and the first portable auto-scaling radiation detector dosimeter. First responder command control applications to provide for reporting of field measurements and downloading of command instructions to field personnel. Military applications including troop monitoring, deployment and command control. Commercial applications include remote environmental data collection and employee assignment tasking.

BRIEF DESCRIPTION OF THE DRAWINGS

FIG. 2 is a left side view of the portable personal safety indicator.

FIG. 3 is a right side view of the portable personal safety indicator.

FIG. 4 is a top view of the portable personal safety indicator.

FIG. 5 is a bottom view of the portable personal safety indicator.

DETAILED DESCRIPTION

The described embodiment(s) of the structures and method are described herein and unless specifically noted, it is intended that the words and phrases in the specification and claims be given the ordinary dictionary or accustomed meaning to those of ordinary skilled artisans. If any other meaning is intended, that special meaning applied to a word or phrase will be specifically stated. It is intended that the inventions not be limited only to the specific structure, material or methods that are described in the preferred embodiments, but in addition, include any and all structures, materials or methods that perform the claimed function, along with any and all known or developed subsequently equivalent structures, materials or methods for performing the claimed function.

The attached FIGS. 1 through 7 illustrate a portable personal safety indicator 25 operating for real time personal safety monitoring by testing the environment for conditions that may be detrimental to an individual's health and for reporting those conditions and measurements including the individual's physiology of the individual.

Figure 1:
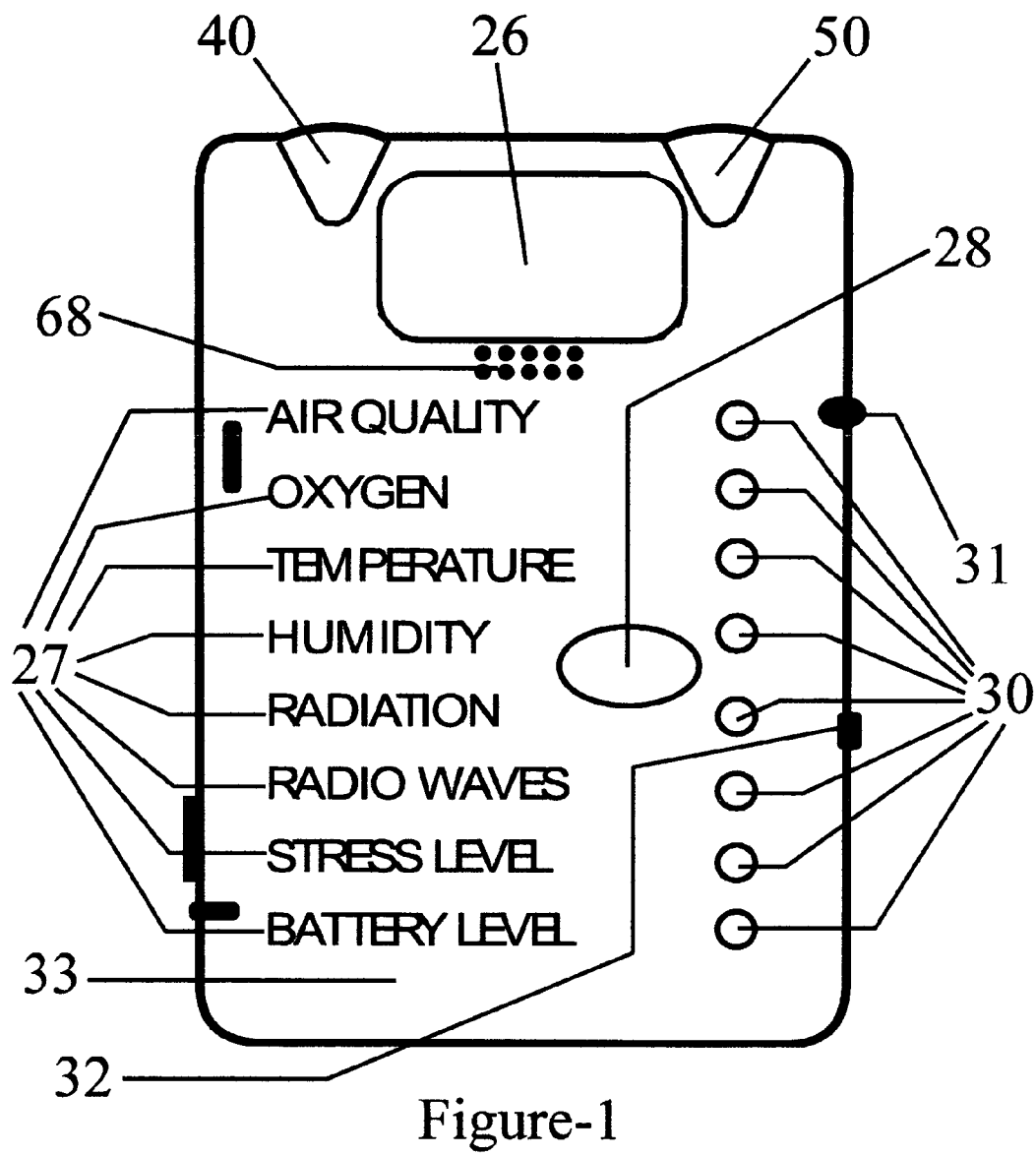
FIG. 1 is a front view of the portable personal safety indicator.

According to one embodiment of the preferred portable personal safety indicator 25 there is an alphanumeric liquid crystal display, herein "LCD" display 26 consisting of two lines of eight characters in each as depicted in FIG. 1. LCD display 26 is backlit for low light applications and the contrast may be adjusted via operation settings selected by the operator from a main menu 88 illustrated in FIG. 19.

Environmental alarm legends 27 shown in FIG. 1, and associated alarm light emitting diodes, herein "LEDS" 30 indicate detected environmental alarm conditions observable by user. Present measurements of a given environmental condition reaches alarm status signaling of, for example but not by way of limitation, air quality, oxygen, temperature, humidity, air pressure, radiation, radio waves as measured electromotive force herein "EMF" or physiological human stress levels is given by audio herein speaker 28. LCD display 26 or LEDS 30, shown in FIG. 1 or vibrator 150 shown only as a block in FIG. 22. Alarm conditions are predetermined by factory default settings or user specified settings at which point portable personal safety indicator 25 will signal alarm condition(s).

Alarms may be indicated by vibrator 150 if hidden silent operation is selected. Flashing of appropriate alarm LEDS 30 is preferred. If more than one alarm condition is present, then multiple alarms may be shown by individual LEDS 30 that will thereby be illuminated or flashed indicating appropriate warnings. In the preferred circumstance, LCD display 26 will show the current measurement for the alarm condition(s) indicative of the hazard associated with alarm LEDS 30 being constantly lit for a period of five seconds. Any of the other alarm LEDS 30 that is active will be flashing. Portable personal safety indicator 25 will display all alarm condition measurements on LCD display 26 in a round-robin fashion until the user turns the alarm state to off by depressing a push button array 31 shown in FIG. 3 twice within two seconds thereby clearing each alarm condition signal. Push button array 31 is used to select user options and for all users initiated functions as will be described. Switch 32 also shown in FIG. 3, controls the on or off power to the portable personal safety indicator 25 also in FIG. 3.

Figure 6:
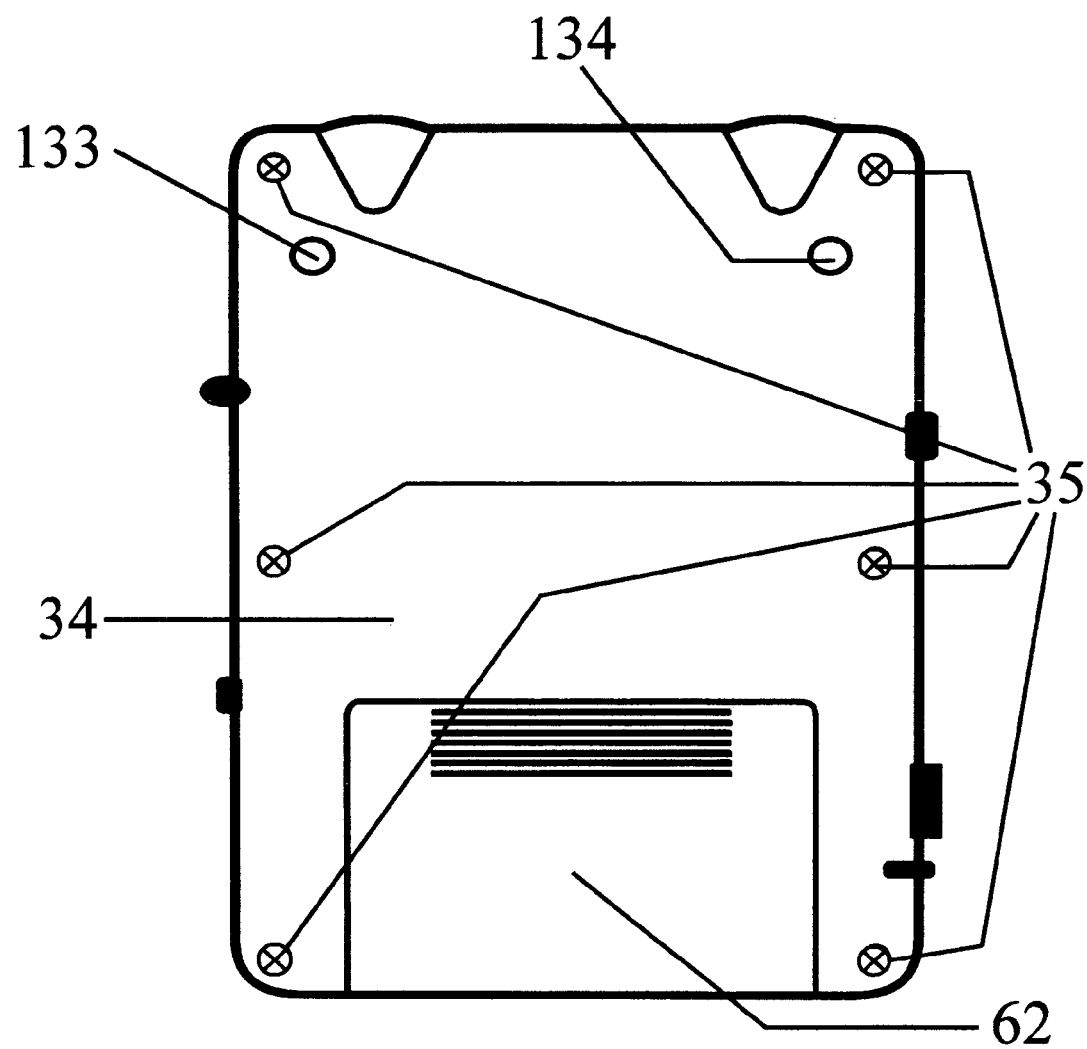
FIG. 6 is a rear view of the portable personal safety indicator.
Figure 7:
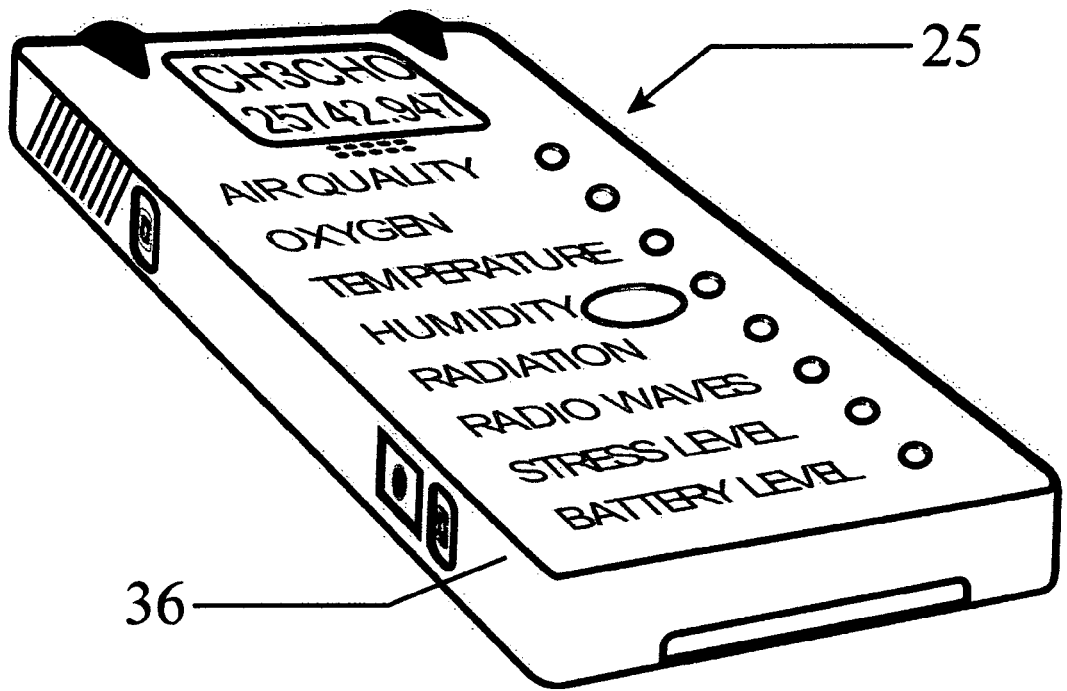
FIG. 7 is a perspective view of the portable personal safety indicator.

A gas sensor 40 depicted in FIG. 4 provides for continuous measurement of air borne agents. An oxygen sensor 50 provides for continuous measurement of ambient oxygen levels. To house portable personal safety indicator 25, a top case 33 illustrated in FIGS. 1, 2, 3, 4, 5 and 6 is attached to a bottom case 34 shown in FIG. 6 are provided and held together by six assembly screws 35. Thus the portable personal safety indicator 25 is packaged in a plastic clam shell shaped case 36 depicted in FIG. 7 that is secured with 6 screws. Case 36 has a left vent 37 shown in FIG. 2 and a center vent 38 illustrated in top view FIG. 4 to create a path for cross ventilation air flow for gas sensor 40. Similarly a right vent 39 shown in FIG. 3 and center vent 38 create a path for cross ventilation air flow for oxygen sensor 50. FIG. 7 depicts in a perspective view of portable personal safety indicator 25 as a small, lightweight and therefore compact device with an approximate size of 2-¼ inches or 5.7 centimeters wide by 3-½ inches or 8.9 centimeters high by 1 inch or 2.5 centimeters thick with weight and construction characteristics similar to typical state of the art multifunction cell phones. The preferred embodiment consists of a charcoal gray plastic for case 36 with silkscreen legends in black and neon blue borders.

Accessible on case 36 is a headphone jack 60 shown in FIG. 2 and it is provided for external audio via a headset 61 plugged into headphone jack 60 and in the alternative fashion either speaker 28 or headset 61 is disabled when the other is used. Also as with portable battery powered equipment there is a power jack 63, in FIG. 2, that provides access for a power source 64 in FIG. 17 typically having a transformer and rectifier 65. Power jack 63 is for direct use or recharging the battery pack 66 depicted in FIG. 17 also behind door 62 in FIG. 6. Battery pack 66 includes cells adequate, such as quantity three 1.2 volt AAA Panasonic Nickel-Metal Hydride 700 mAh part# HHR-75AAA available from distributor Digi-Key Corporation, Thief River Falls, Minn., that provide for up to thirty two hours of continuous operation per charge. Microphone 68 shown in FIG. 1 provides for audio input for digital recording functions and sound pressure measurements in decibles. Recordings, music, stored voice prompts and audio alarms can be played through speaker 28. The speaker 28 volume and microphone 68 sensitivity may be adjusted via the main user main menu 88.

Portable personal safety indicator 25 is typically worn by the user externally, using a clip to attach to a belt, pocket or shirt lapel. Other common wearing applications may use holster mounts for wear or attachment to a vehicle dash for vehicle safety applications or for leaving plugged into an AC wall outlet for home or office applications in addition to hand held use. While none of the manner of wearing are specifically shown they are common in other portable devices and thus understood by artisans and users.

The internal assembly of portable personal safety indicator 25 consists of several circuit boards layered in a stack configuration with header interconnects between layers. Circuit board construction is predominately type-2 surface mount technology with components mounted on both sides of each circuit board. Since these techniques are well known in the industry, further description or drawings will not be provided in this disclosure. The combination of type-2 construction, layered boards and miniature surface mount components allow for a large number of product functions to be incorporated in a small, lightweight package. Specific circuits are in the block diagrams of the drawings and the descriptions related thereto.

Figure 8:
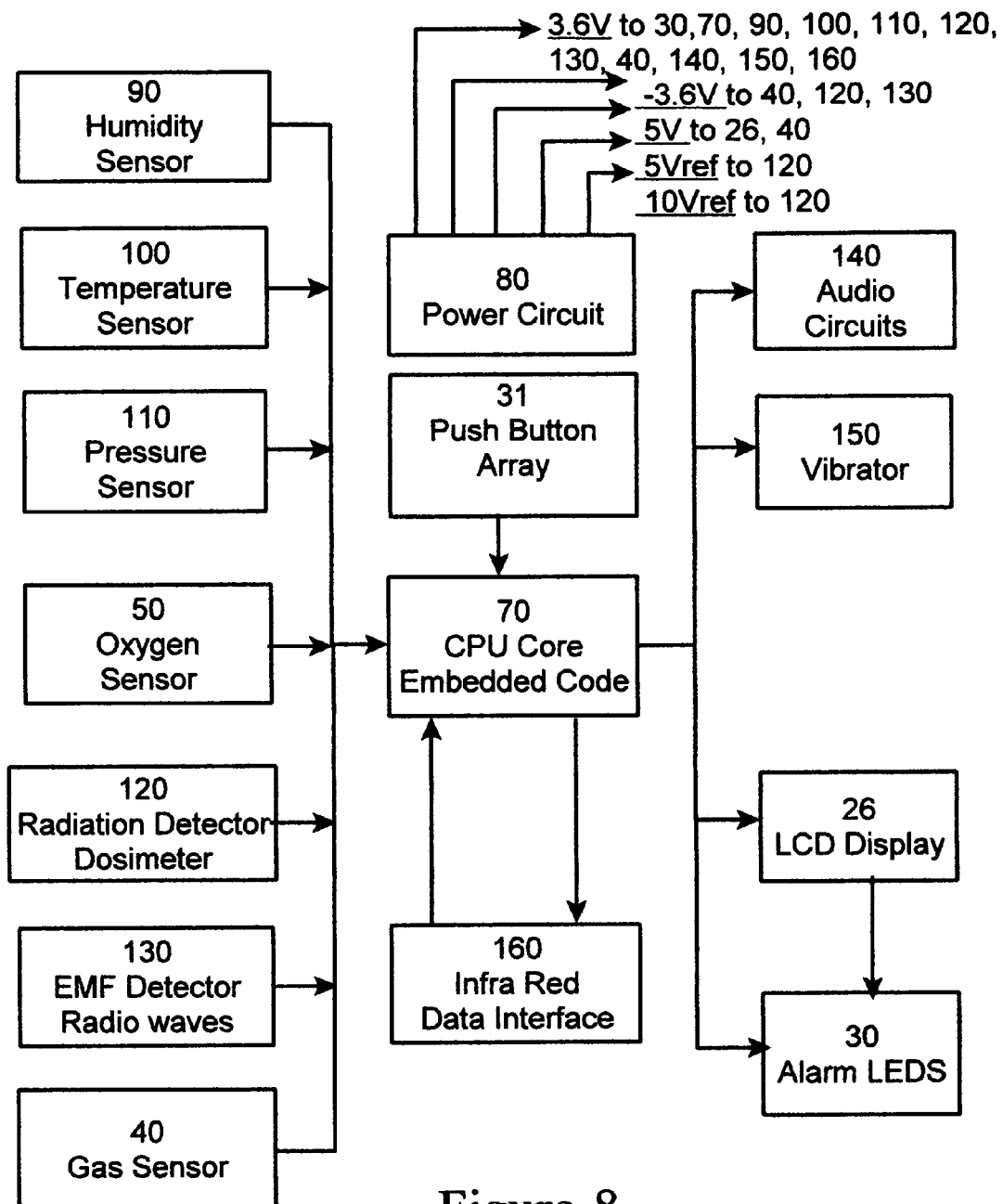
FIG. 8 is a block diagram in showing the relationship of the various circuits that are also shown as blocks.

The theory of operation of the portable personal safety indicator 25 is quickly understood with reference to FIG. 8, a block diagram. Embedded code in a central processor, herein "CPU" having a core 70 controls all operating functions of portable personal safety indicator 25. Power circuit 80 provides for all operating voltages and reference voltages needed by all circuitry. The CPU core 70 continuously monitors input sensors consisting of humidity sensor 90, temperature sensor 100, pressure sensor 110, oxygen sensor 50, radiation sensor 120, EMF detector 130 and gas sensor 40 as transducers for real time measurements of the associated environmental conditions. The preferred sensors and their connections to power circuit 80 and reference voltages are shown in the top right hand corner of FIG. 8 along with the listed voltage and following list of reference numbers for the sensor blocks to which each voltage is provided.

Figure 14:
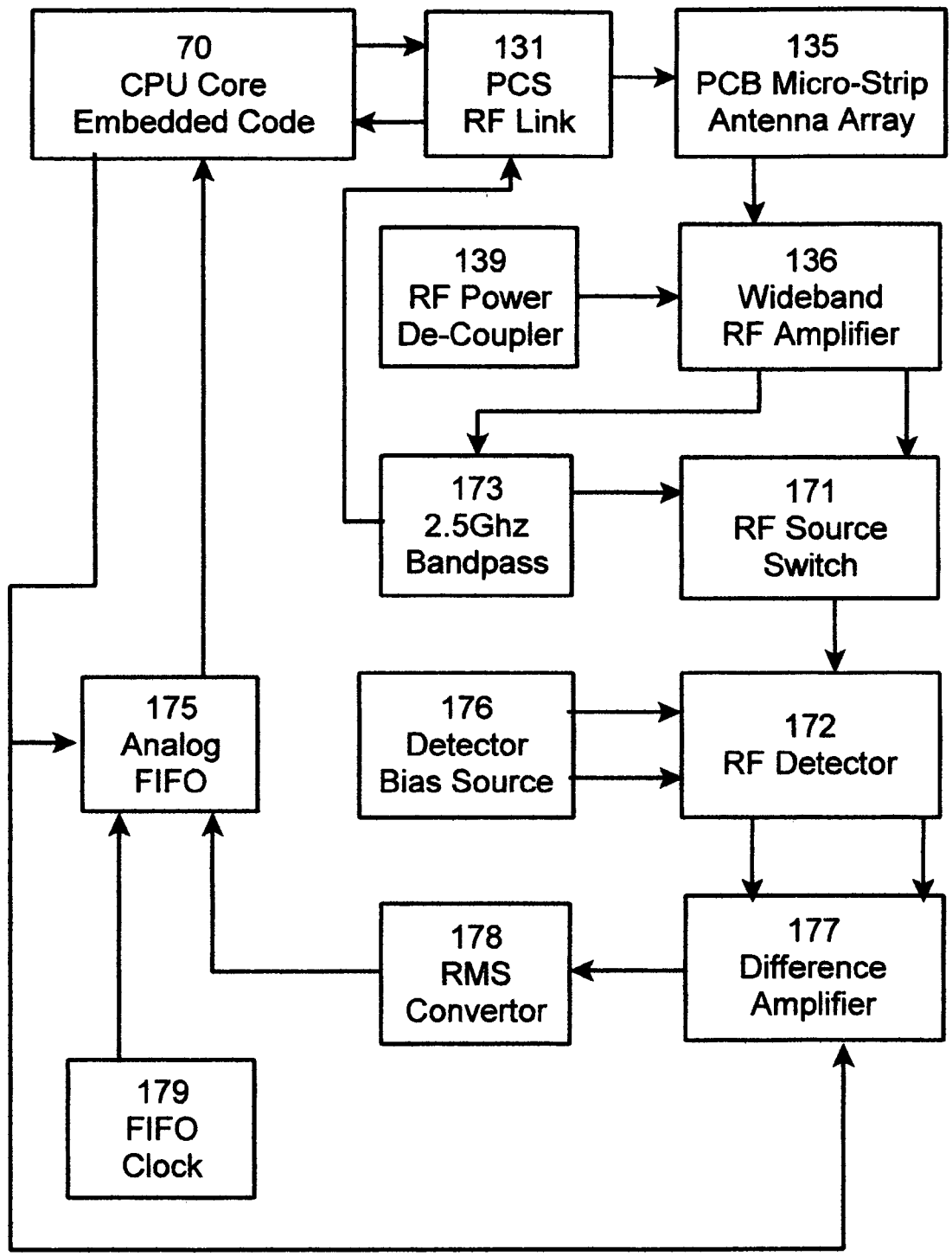
FIG. 14 is an EMF detector dosimeter shown as block diagrams of circuits for that function and operation.

Depending on real time measurements and associated alarm set points, alarms and associated measurements are indicated via various output circuits including audio circuits 140, vibrator 150, LCD display 26 and alarm LEDS 30. User inputs to portable personal safety indicator 25 for control thereof are accomplished via push button 31. This is shown in a FIGS. 3, 8 and 18. External communication with portable personal safety indicator 25 may be accomplished through an infra red data interface 160 or a sub-section of the EMF detector 130 which forms a full duplex PCS RF link 131 described further hereinafter in this disclosure and is shown in FIG. 14. All external communication is controlled and directed by the CPU core 70.

Figure 20:
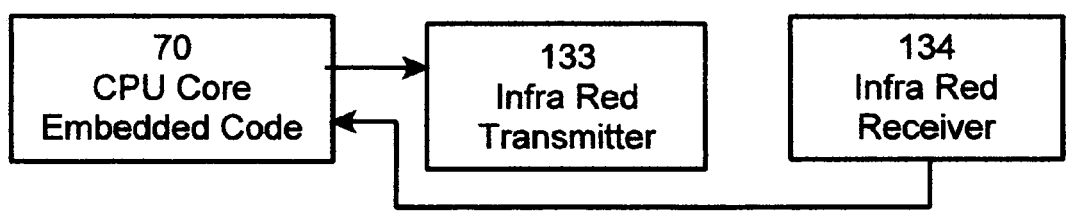
FIG. 20 is an infra red data interface shown as block diagrams of circuits for that function and operation.

Referring to block diagram FIG. 20, infra red transmitter 133 and infra red receiver 134 are infra red data interface 160 for uploading or downloading data to a personal computer, herein "PC". The personal computer may be located anywhere. Data can also be exchanged with any other portable personal safety indicator 25 by infra red data interface 160. Typical computer interface cables and plugs are well known but infra red data interface 160 exchange is preferred.

Figure 9:
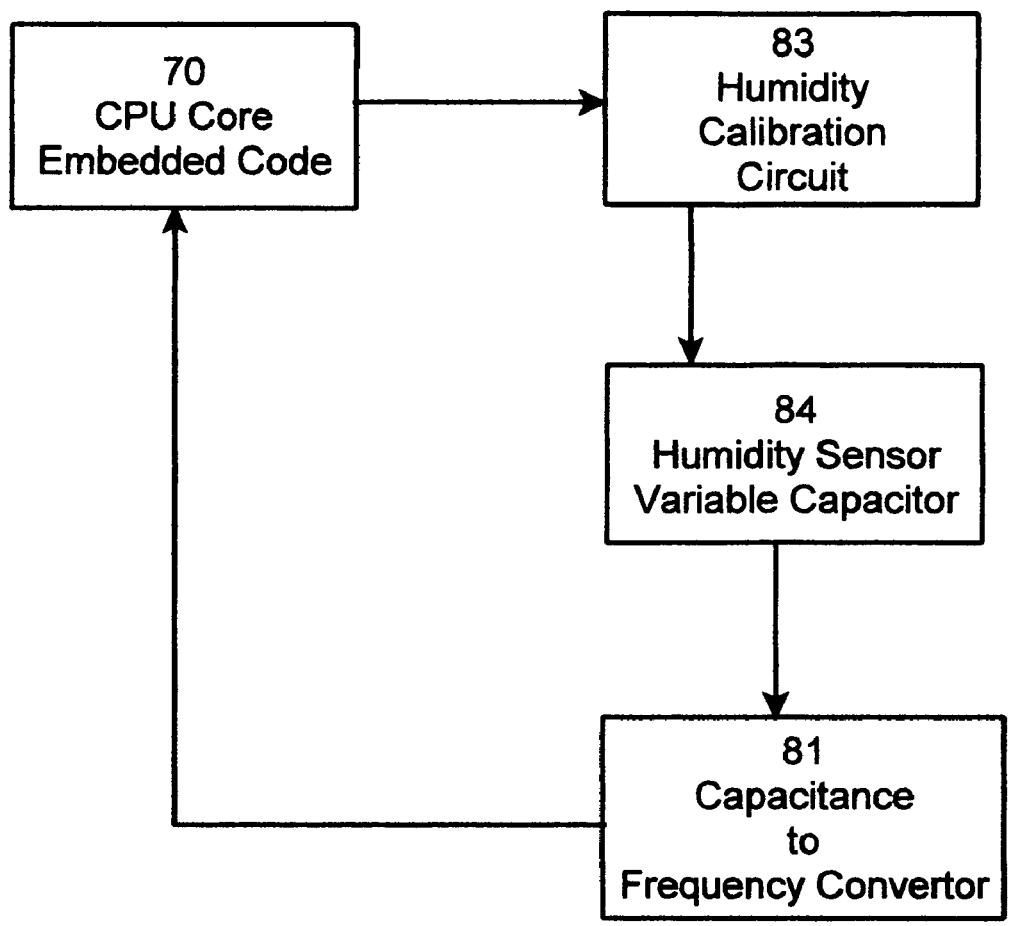
FIG. 9 is a humidity sensor shown as block diagrams of circuits for that function and operation.

Referring to block diagram FIG. 9, humidity sensor 90, operates as follows: humidity measurements are determined by the frequency generated by a capacitance to frequency converter 81. CPU core 70 initiates a humidity measurement by reading the frequency output from the capacitance to frequency converter 81. The frequency output from capacitance to frequency converter 81 is measured by CPU core 70 and that value is used as an index into a humidity lookup table 82 to determine the actual humidity measurement following normalization procedures. Humidity sensor 90 acts as a variable capacitor 84 shifting as a function of actual relative humidity. The current embodiment uses commercial sensor 2322 691 90001 obtained from The Vishay Company located in Malvern, Pa.; this particular humidity sensor 90 is capable of measuring 10 to 90% relative humidity based on a typical 0.4 pico farad change in sensor capacitance per one percent change in relative humidity. Humidity calibration circuit 83 and variable capacitor 84 of humidity sensor 90 form a resistance capacitance, herein "RC" timing network which controls the pulse width generated by capacitance to output frequency converter 81. Humidity lookup table 82 in CPU core 70 is for a humidity calibration circuit 83 shown in FIG. 9. Determining the capacitance change per percent change of relative humidity at 0%, 43.2% and 75.3% relative humidity at 25 degrees centigrade is the calibration. Specifically, the output frequency from capacitance to frequency converter 81 is measured with portable personal safety indicator 25 in a vacuum which is equivalent to 0% relative humidity. To calibrate potassium carbonate salt is used to subject the portable personal safety indicator 25 to an environment of 43.2% relative humidity so the output frequency from capacitance to frequency converter 81 can be measured. Similarly with sodium chloride salt, the portable personal safety indicator 25 is subjected to an environment of 75.3% relative humidity. Those three measurements are stored in non volatile memory of CPU core 70. Using these output frequency measurements, humidity lookup table 82 is built by extrapolating the delta capacitance change per percent change in relative humidity. Humidity lookup table 82 is stored in nonvolatile memory of CPU core 70. The capacitance of humidity sensor 90 also varies with temperature, however, this variance is predictable and a normalization table is stored in non volatile memory of CPU Core 70 to instantaneously adjust in real time any readings.

Figure 10:
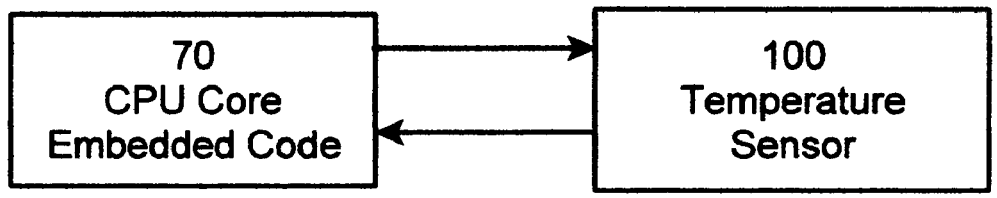
FIG. 10 is a temperature sensor shown as block diagrams of circuits for that function and operation.
Figure 11:
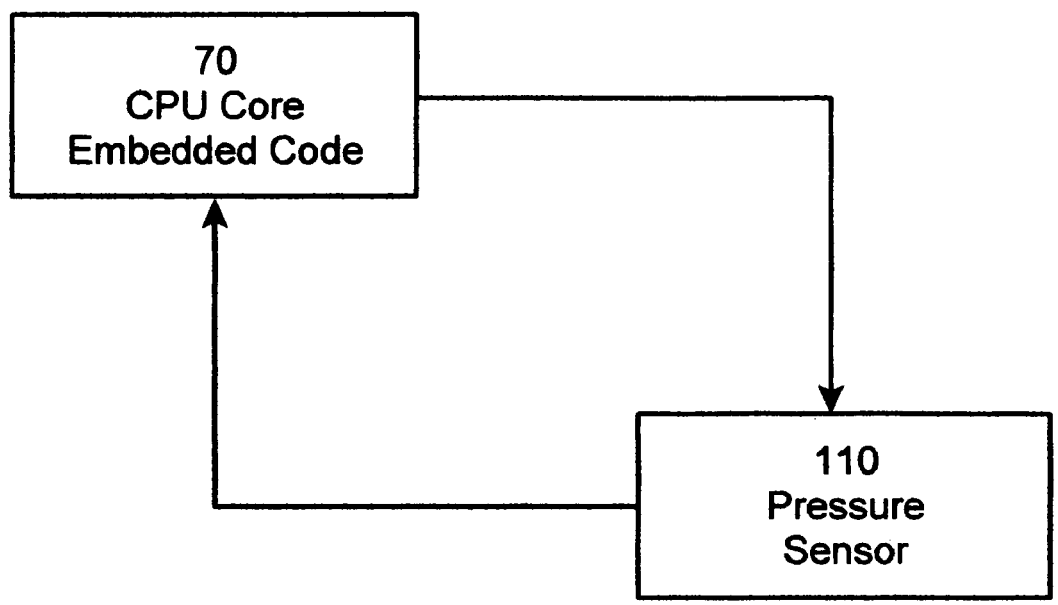
FIG. 11 is a pressure sensor shown as block diagrams of circuits for that function and operation.
Figure 12:
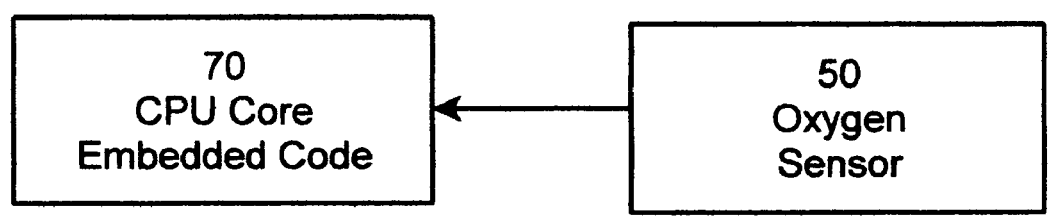
FIG. 12 is an oxygen sensor shown as block diagrams of circuits for that function and operation.
Figure 13:
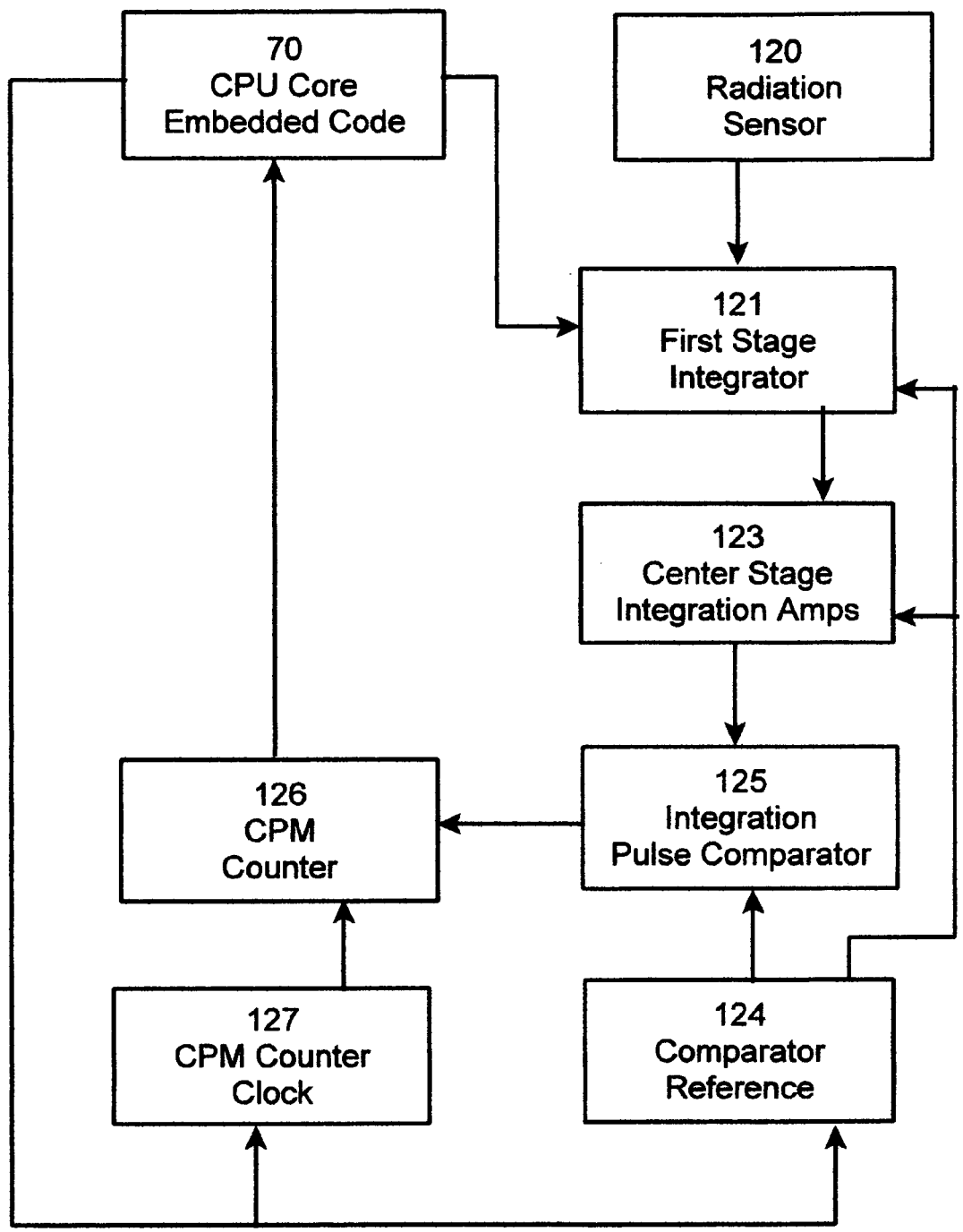
FIG. 13 is a radiation detector shown as block diagrams of circuits for that function and operation.

Characteristics of humidity sensor 90 may also vary slightly after several years of operation. For this reason, the embedded code of CPU core 70 allows for user field calibration by inputting a humidity reading from an accurate local source. In that case, the humidity calibration circuit 83 is reprogrammed to normalize subsequent readings. The current embodiment allows for an accuracy reading of plus or minus 1% of actual relative humidity. Referring to block diagram FIG. 10 for temperature sensor 100 indicates that temperature measurements are initiated by CPU core 70 requesting a conversion from preferably a single chip semiconductor sensor temperature sensor 100 such as but not limited to, the DS1629 which includes Date and Time functions also used for time-stamping real time measurements, and is made and sold by Dallas Semiconductor/Maxim located in Cavite, Philippines. CPU core 70 subsequently reads out the temperature conversion value from the reading of the temperature sensor 100. Temperature sensor 100 is capable of measuring ambient temperature from −55 to +125 degrees centigrade with an accuracy of plus or minus 0.5 degrees centigrade. Again the conversion value is used as an index to a temperature lookup table 101 contained in non volatile memory of CPU Core 70 to obtain the actual temperature value. Field calibration can be accomplished by the user inputting actual temperature from a reliable and accurate source. In that case, temperature lookup table 101, located in the CPU core 70 internal memory is modified to provide for subsequent normalized readings. In block diagram FIG. 11 wherein pressure sensor 110 for ambient barometric pressure measurements initiates by conversion requests from CPU core 70 to pressure sensor 110. Pressure sensor 110 is preferably a highly integrated single chip device packaged in vacuum enclosed by a flexible diaphragm cover such as but not limited to the MS5534 commercially available from Servoflow Corporation located in Lexington, Mass. Changes in barometric pressure cause the pressure in the vacuum to change due to motion in the flexible diaphragm cover. These changes are detected by pressure sensor 110 including a silicon chip integral with pressure sensor 110 which in turn is reflected by variations in conversion values. The current embodiment using the MS5534 is capable of measuring barometric pressure from 750 to 1100 mbar with a resolution of 0.1 mbar and an accuracy of +/−0.5 mbar. Since temperature can affect the internal nominal pressure of the pressure sensor 110 depending on which type of pressure sensor is used as is the specific case for the MS5534, temperature dependant coefficients are measured at the factory and stored in non volatile memory located in pressure sensor 110. Those coefficients are subsequently used in a correction algorithm during real time measurements to normalize the reading; thus field recalibration is not required. The combination, of pressure sensor 110, temperature sensor 100, humidity sensor 90, EMF detector and embedded code in CPU core 70, forms the basis for a portable weather measuring station which may be used to log and predict local weather changes. Embedded weather station software located in CPU Core 70 incorporates sensor readings (lightning) from the EMF detector 130 to foretell dangerous weather conditions. Referring to block diagram FIG. 12 wherein oxygen sensor 50 constantly monitors ambient oxygen levels and oxygen level measurements are made by CPU core 70 as A/D conversions of the measured current analog voltage value received from oxygen sensor 50. In particular, the current embodiment, oxygen sensor 50 functions as a galvanic cell (battery), whose output voltage is directly related to the amount of ambient oxygen levels. The output voltage of oxygen sensor 50 varies from over the range of 0 to 100% with respect to measured ambient oxygen percentage. The characteristics of the oxygen sensor 50 are linear and the analog voltage readout is used as an index into an oxygen lookup table 51 residing in CPU core 70 to obtain an interim oxygen % reading. That oxygen sensor 50 is from Figaro, located in Glenview, Ill. Output voltage levels from oxygen sensor 50 are affected by barometric pressure, temperature and humidity; normalization lookup tables for the particular sensor are consulted by embedded code in the CPU core 70 using concurrent readings from humidity sensor 90, temperature sensor 100 and pressure sensor 110 to obtain an accurate instantaneous ambient oxygen measurement. Oxygen sensor 50 is capable of measuring ambient oxygen levels from 0 to 100% with an accuracy of +/−1%. Referring to block diagram FIG. 13, radiation detector having a radiation sensor 120 consisting of a pin photodiode with preferably a comparatively large surface area for a depletion region created by reverse biasing the pin photodiode. When a radioactive particle, alpha or beta, a photon, gamma or x-ray collides with the depletion region, it produces an associated charge increase in the depletion region in proportion to the energy imparted from the particle or photon. Radiation sensor 120 is thereby capable of detecting alpha, beta, gamma and x-ray radiation. The current embodiment uses a BPW34 pin photodiode as radiation sensor 120 and is commercially available from the Siemens Semiconductor Group. The associated charge is delivered to a first stage integrator 121 that includes a variable gain analog amplifier whose AC signal gain characteristics are digitally controlled by CPU core 70. This allows first stage integrator 121 to be auto scaling so saturation of first stage integrator 121 does not occur, which in turn, allows for accurate instantaneous radiation level measurements. First stage integrator 121 can be programmed by CPU core 70 to respond at a rate of up to 3,000,000 collisions per minute (CPM, counts per minute), which is equal to an exposure rate of 3000 mR/hr. First stage integrator 121 and a center stage integration amps 123 provide for a combined signal gain of 10,000. A comparator reference voltage circuit 124 provides a trigger reference voltage to first stage integrator 121, center stage integration amps 123 and an integration pulse comparator 125. A comparator reference voltage 124 acts as a noise gate to eliminate potential background noise from generating spurious CPM pulses. Comparator reference voltage 124 in FIG. 13 is digitally controlled by CPU core 70 to obtain the optimum trigger reference voltage.

Charge increases from radiation sensor 120 are amplified and converted into a digital pulse of varying time duration proportional to the charge increase by integration pulse comparator 125. A digital pulse from integration pulse comparator 125 acts as a clock enable gate 122 for a CPM counter 126 that counts clock pulses from a CPM counter clock 127 while clock enable gate 122 signal is active. The time period and frequency of clock pulses from CPM counter clock 127 is digitally controlled by CPU core 70. That relationship is such that for a given gain setting of first stage integrator 121, CPM counter clock 127 is configured to cause an accurate CPM count by CPM counter 126. Since multiple collisions of various energy levels can occur simultaneously in the depletion region of radiation sensor 120, the preceding gain adjustment of first stage integrator 121 and comparator reference voltage circuit 124 allows for more accurate measurement of effective radiation exposure rates when compared to current techniques. CPM counter 126 generates an interrupt to CPU core 70 when its count value is greater than zero. CPU core 70 in turn reads out the current count value of CPM counter 126 and stores this count value and an associated time mark in nonvolatile memory of CPU core 70. The process of reading out the count value clears CPM counter 126 allowing for subsequent counting. The preceding concept allows CPU core 70 to process multiple sensor readings simultaneously without missing critical data. Up to three months of radiation level measurements and exposure times are stored in non volatile memory of CPU core 70. This data can be read out for various report functions. In this manner, the portable personal safety indicator 25 functions with auto scaling radiation detection with several times the measurement bandwidth of typical current product offerings and as a radiation dosimeter.

Referring to block diagram FIG. 14 EMF detector 130 includes printed circuit boards herein, PCB micro-strip 135 consists of an array of tuned PCB based micro-strip antennas designed to cover the frequency range of, 100 KHz to 20 Ghz. A wideband RF amplifier 136 provides for variable gain characteristics versus received signal frequency from PCB micro-strip 135. Wideband RF amplifier 136 is designed to provide increasing gain as the received signal increases in frequency to provide for a more linear output over the frequency operating range of 100 KHz to 20 GHz.

RF power de-coupler 139 provides source power to wideband RF amplifier 136 to de-couple RF power rail current spikes from other circuits of the portable personal safety indicator 25 in order to maintain accurate measurements of all sensors. In addition, RF power de-coupler 139 blocks power rail spikes from other circuits that may affect accurate EMF measurements.

A RF source switch 171 passes the amplified RF signal to an RF detector 172 as directed by CPU core 70. RF detector 172 will receive a signal from a 2.5 GHz bandpass 173 or from the wideband RF amplifier 136 as directed by CPU core 70. The characteristics of 2.5 Ghz bandpass 173 are such that signals may be specifically targeted and measured from various devices including common communication devices including PCS cell phones, microwave ovens, wireless network transceivers and wireless video surveillance devices. This feature allows for accurate measurements of cell phone output power which has been linked to a potential cause of brain tumors due to soft tissue damage. It is fairly common for cell phone antennas to become damaged due to dropping or mishandling. Such damage can cause the cell phone to transmit a much stronger near field signal, which in turn, can cause soft tissue damage with repeated exposure. Other common causes of excessive cell phone emissions include user installed antenna boosters. Portable personal safety indicator 25 can be used to identify cell phones that are transmitting excessive signals which may not be safe for human use. This feature also provides for detection and area location of leaky microwave ovens whose emissions exceed published safety standards which can cause significant soft tissue damage and interference with other electronic devices including pacemakers. Due to the storage characteristics of an analog FIFO 175 which is a first in first out analog storage device and embedded code in CPU core 70 this feature may also be used to locate common hidden wireless video surveillance devices.

RF detector 172 converts the RF-AC signal received from RF source switch 171 into a proportional DC voltage based on the RF-AC signal amplitude received. This is accomplished in RF detector 172 using its matched set of microwave detector diodes operating in a nonlinear junction resistance mode. A detector bias source 176 provides forward bias currents to RF detector 172 detector diodes to insure that RF-AC signals are immediately detected and converted into a proportional DC voltage. Ambient temperature changes create significant non linear output variations from the RF detector 172 detector diodes. This characteristic is corrected by using a matched set of RF detector 172 detector diodes where one diode is used to convert the RF-AC signal into a DC voltage which feeds one side of a difference amplifier 177 and the other diode, without signal, feeds the other input of difference amplifier 177. The result is a fairly linear output from difference amplifier 177 corrected for temperature variations. RF detector 172 operates over the frequency range of 100 KHz to 20 GHz. The gain of difference amplifier 177 is digitally controlled by CPU core 70 to provide for auto scaling of EMF detector 130.

When CPU core 70 detects a maximum measured level from analog FIFO 175, the gain of difference amplifier 177 is reduced and scaled to insure that circuit saturation does not cause missed data or inaccurate EMF measurements. The programmable gain characteristics of difference amplifier 177 are such that portable personal safety indicator 25 can detect and measure EMF (power density) levels ranging from one nano watt to ten watts RMS/cm$^2$. A RMS converter 178 receives a DC signal with a small AC component from difference amplifier 177; this signal is converted into a DC voltage level that is representative of the RMS signal level received and this value is stored in analog FIFO 175 and passed onto CPU core 70. Using current scale factors and a normalization lookup table, CPU core 70 converts this DC voltage into a final RF RMS measurement.

Analog FIFO 175 functions as a first in first-out analog sample and hold circuit. CPU core 70 digitally controls the minimum threshold level for enabling storage of analog samples received from RMS converter 178. Provided the minimum threshold level is met, clock pulses from a FIFO clock 179 are used to clock analog samples from RMS converter 178 into analog FIFO 175. Once an analog value has been stored in analog FIFO 175, an interrupt is generated from analog FIFO 175 to CPU core 70 and that responds by reading out all stored analog values from analog FIFO 175 and stores these measurements along with a time stamp into non volatile memory of CPU core 70. Reading out of analog FIFO 175 also clears it allowing for subsequent measurements. The preceding concept allows CPU core 70 to process multiple sensor readings simultaneously without missing critical data. Up to three months of stored values are retained for subsequent readout for reporting purposes. In the manner previously described portable personal safety indicator 25 functions as an EMF detector 130, power density field meter and provides for a new innovative function called, an "EMF dosimeter". At high sensitivity settings, portable personal safety indicator 25 also functions as an electronic bug detector. In that mode, it can be used to detect various wireless or hardwired audio and video surveillance devices. PCS RF link 131 provides for full duplex remote communications via an external PCS cell phone. CPU core 70 initiates GMS (a global system for mobile communication that is supported worldwide) cell phone calls or requests current GPS coordinates by utilizing PCS RF link 131. PCS RF link 131 uses a portion of PCB micro-strip 135 to serve as its transmitting antenna operating at an approximate base frequency of 2.5 GHz utilizing typical a RF FSK, "frequency shift keying" modem concepts which are widely known and as such will not be described herein. An optional adaptor 180 is attached to the external PCS cell phone to complete the RF FSK communications channel. Received RF FSK data is passed from 2.5 GHz bandpass 173 to PCS RF link 131 which in turn passes this demodulated data to CPU core 70. A start ID, "identification" pattern 181 and an end of data packet CRC 182 (cyclic redundancy code used for error checking of data packets) are used to insure that only valid data packets are received. Each portable personal safety indicator 25 has a unique embedded serial number which is used to generate a unique start-ID pattern. Received start-ID patterns which do not match any embedded serial number of portable personal safety indicator 25 are ignored. Portable personal safety indicator 25 does use the reception of other valid start-ID patterns to adjust its transmit timing to avoid PCS RF link 131 data collisions with any other portable personal safety indicator 25. PCS RF link 131 is primarily intended for first responder command control applications to provide for uploading of alarm conditions, field measurements and downloading of command instructions to field personnel, military applications including troop monitoring, deployment and command control, common commercial applications including remote environmental data collection, employee assignment tasking and consumer or commercial voice mail applications. PCS RF link 131 supports reception of real time data for remote monitoring of personnel via the optional wrist band bio-monitor. The wrist band bio-monitor periodically samples the wearer's blood pressure, temperature, pulse rate and blood oxygen levels and transmits this data to portable personal safety indicator 25. Measurements of the preceding can be initiated by wrist band bio-monitor if significant changes are detected in body temperature or pulse or by portable personal safety indicator 25 at anytime according to application. Typical applications for this feature include critical monitoring of field personnel for first responder and military applications and remote medical patient monitoring. This combination of portable personal safety indicator 25 environmental measurements and wrist band bio-monitor provide for a new feature of environmental cause affect reporting. The optional wrist band bio-monitor contains a parallel array of infrared transmitters and infrared receivers positioned at 90 degrees to each other and the device seeks the highest blood flow area of the wrist which is to be used for pulse, temperature, blood pressure and blood oxygen measurements by sequentially turning on a IR transmitter followed by monitoring it's counterpart receiver. The transmit/receive pair which exhibits the highest level of IR absorption consistent with a typical pulse rate is used for measurements as this pair is most likely located over a major artery. Blood oxygen levels are measured by detecting the level of infrared absorption that occurs during major variations in blood area content which is consistent with a nominal pulse and hemoglobin concentration. The IR transmitter/receiver array allows the wrist band bio-monitor to be self seeking and self calibrating in looking for the best location to monitor vital functions. Wrist band held monitoring devices are common thus not specifically shown or described.

GPS coordinates received from PCS RF link 131 can be used for remotely locating personnel and reporting coordinates associated with alarm occurrences and associated environmental measurements. Up to three months of GPS coordinate data can be stored and associated with portable personal safety indicator 25 environmental or wrist band bio-monitor biological measurements in the non volatile memory of CPU core 70 for subsequent reporting functions.

Figure 15:
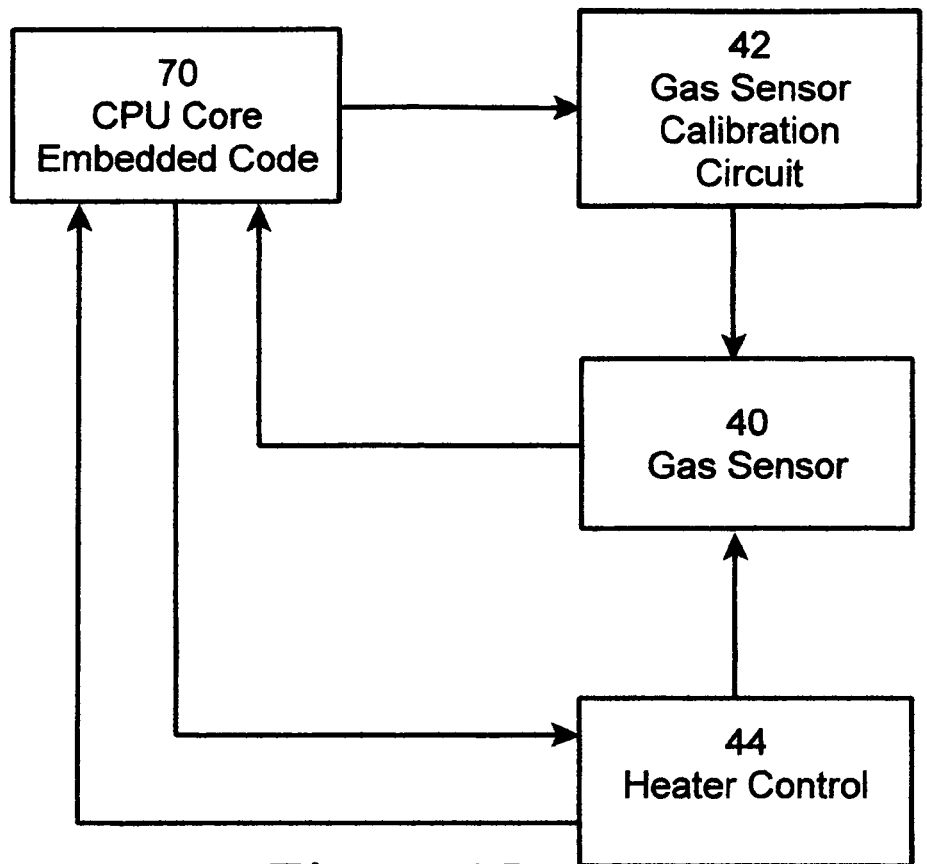
FIG. 15 is a gas sensor shown as block diagrams of circuits for that function and operation.
Figure 16:
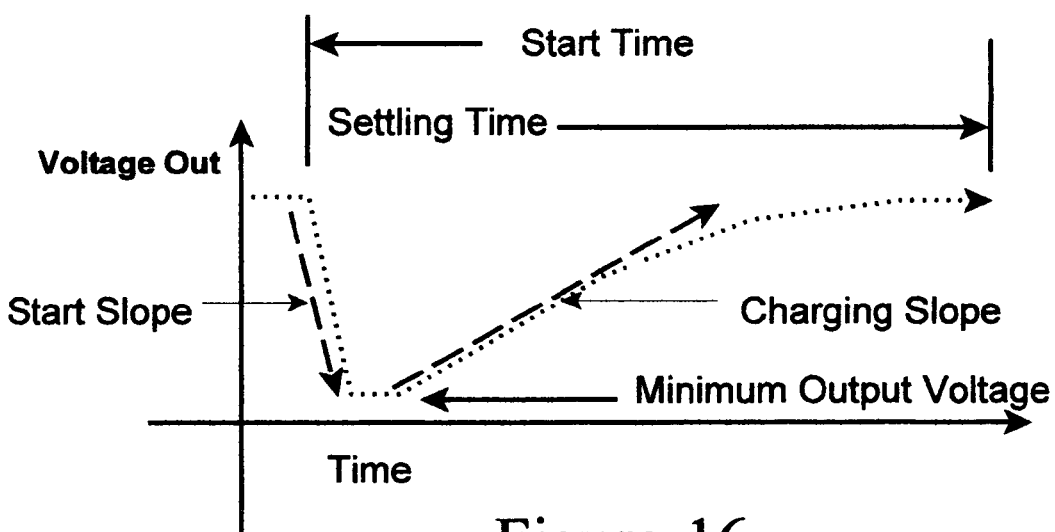
FIG. 16 is a graphical plot of an initial start slope, start time to minimum output voltage, charging slope and settling time which form the data for an individual associated detection response curve of a gas sensor such as that in FIG. 15.

Referring to block diagram FIG. 15 gas sensor 40 wherein gas sensor 40 continuously monitors ambient air for contaminants and an associated output voltage from gas sensor 40 is measured by CPU core 70 to determine when contaminants are present. Gas sensor 40 is capable of detecting several hundred different air born contaminants each of which has an individual associated detection response curve. CPU core 70 maintains a lookup table of characteristic individual associated detection response curves in non volatile memory for comparison to real time measurements to help identify air borne contaminants and to perform threat assessment of current environmental conditions. The nature of gas sensor 40 is such that initial exposure to air borne contaminants causes a very significant and rapid decrease in output voltage followed by a slower charging curve with a slope that can be calculated, followed by a final settling time with a time duration that can be measured. Referring to graph plotted as FIG. 16, there is the combination of the initial start slope, start time to minimum output voltage, charging slope and settling time form the data for an individual associated detection response curve. CPU core 70 continuously polls gas sensor 40 to determine when an air borne contaminate has been detected and calculates the Individual associated detection response curve from real time data for subsequent table lookup purposes in gas sensor lookup table 41 which is stored in non volatile memory of CPU core 70. Due to source manufacturing variations in gas sensors, gas sensor 40 has a calibration circuit 42 to normalize sensor variations during portable personal safety indicator 25 factory calibrations. Calibration circuit 42 also provides for field re-calibration of gas sensor 40 which may be required due to natural aging processes of gas sensor 40. During factory calibration, individual characteristics of gas sensor 40 are stored in non volatile memory of CPU core 70. Those characteristics include a fresh air reading which is used for comparison to subsequent field based fresh air readings to track potential aging changes in gas sensor 40. In addition, a calibration gas of known PPM, "parts per million" is used during the factory calibration process and associated measurements of this calibration gas are also stored in non volatile memory of CPU core 70. If significant changes in gas sensor 40 are detected during field based fresh air readings, the user is notified by portable personal safety indicator 25 to use a calibration gas sample for field recalibration. During field recalibration, lookup tables 41 located in nonvolatile memory of CPU core 70 are updated to adjust for characteristic aging changes in gas sensor 40. Gas sensor 40 contains a heater coil 43 that is used to burn off sensor surface contamination that may accumulate due to exposure from air borne contaminates. CPU core 70 uses a heater control 44 to keep gas sensor 40 clean of contaminates. In some cases, gas sensor 40 may become permanently contaminated due to excessive contaminate exposure that can't be removed by heater control 44. In that case, CPU core 70 will notify the user that gas sensor 40 needs to be replaced.

To help conserve battery power, CPU core 70 detects when the portable personal safety indicator 25 is attached to external power source 64 preferably a battery charger and uses these opportunities to accelerate cleaning of gas sensor 40. Gas sensor 40 is packaged in an insulating material to help maintain an elevated sensor temperature with minimum heater current which also serves to conserve battery power during mobile operation. Heater control 44 provides a heater coil 43 okay signal to CPU core 70. That signal is monitored and the user is notified that gas sensor 40 needs to be replaced if heater control 44 detects that heater coil 43 has become defective. Electrochemical cell based gas sensor 40 readings are very sensitive to environmental variations including temperature, humidity, barometric pressure and ambient oxygen levels. It has been determined that the cumulative affect of these environmental variations can affect gas sensor 40 reading accuracy by as much as 420%. Portable personal safety indicator 25 is the first mobile gas sensor 40 that incorporates real time measurement of environmental variances to correct real time gas sensor 40 readings using normalization lookup tables for temperature, humidity, barometric pressure and ambient oxygen levels. The result is the first available accurate gas sensor 40 for mobile applications.

The following is a partial list, by no means to be considered comprehensive; of gases that gas sensor 40 is capable of detecting along with associated detection sensitivity characteristics. H2 "Hydrogen" 1 PPM, (CH3)2CHCH2OH 1 PPM, CO "carbon monoxide" 1 PPM, C2H5OH "ethanol" 1 PPM, (CH3)2CHOH 1 PPM, NH3 "ammonia" 1 PPM, CH3CHO "acetaldehyde" 0.1 PPM, "propionic acid" 1 PPM, C6H5CH3 "toluene" 1 PPM, "methyl disulfide" 1 PPM, C6H4(CH3)2 "xylene" 1 PPM, "methyl sulfide" 1 PPM, C6H6 "benzene" 1 PPM, (CH3)3N "trimethyl amine" 0.1 PPM, CH3COOH "acetic acid" 1 PPM, H5CH2OH "benzyl alcohol" 1 PPM, CH3(CH2)4CH3 "n-Hexane" 1 PPM, (C2H5)2O "diethyl ether" 1 PPM, CH3(CH2)5CH3 "n-heptane" 1 PPM, C5H10 "cyclopentane" 1 PPM, 3(CH2) 6CH3 "n-octane" 1 PPM, HCHO 0.1 PPM, CH3(CH2) 8CH3 "n-decane" 1 PPM, NO 0.1 PPM, CH3(CH2)9CH3 "n-undecane" 1 PPM, No2 0.1 PPM, CH3(CH2)4OH "1-pentanol" 1 PPM, buthy ric acid 0.01 PPM, CH3CH(OH) C2H5 "2-butanol" 1 PPM, "varelic acid" 0.01 PPM, CH3OH "methanol" 1 PPM.

Thus by using a breath-tube adaptor, portable personal safety indicator 25 can be used to measure blood alcohol levels. Other common applications include detecting, measuring, identifying and locating sources of air borne contaminants.

Figure 17:
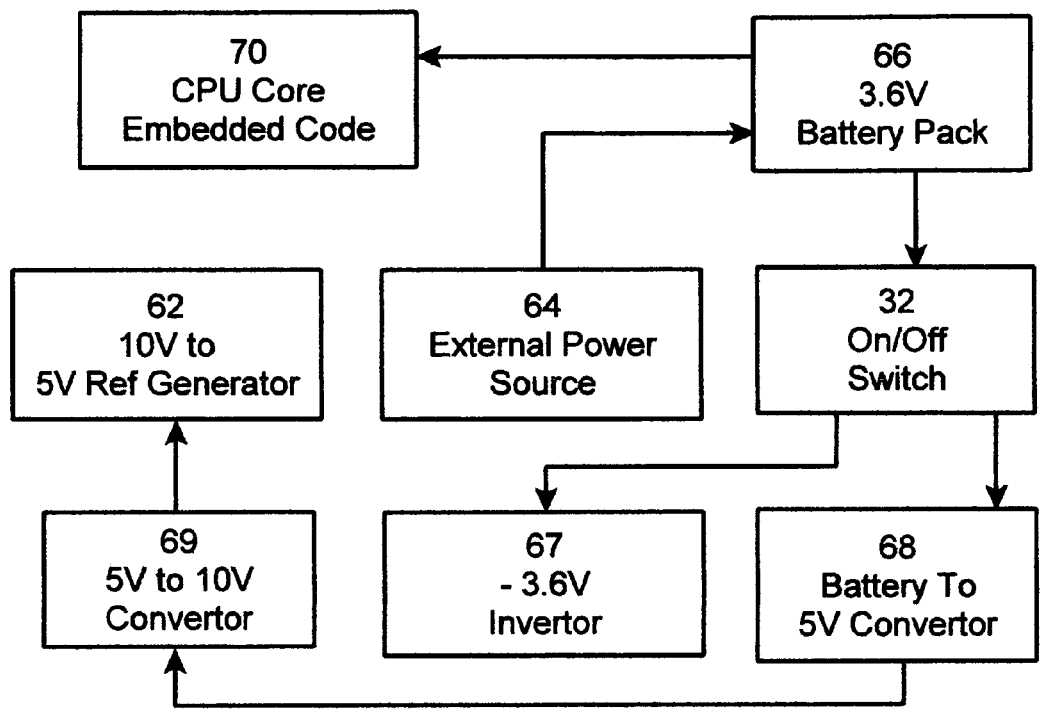
FIG. 17 has power circuits shown as block diagrams of circuits for that function and operation.
Figure 18:
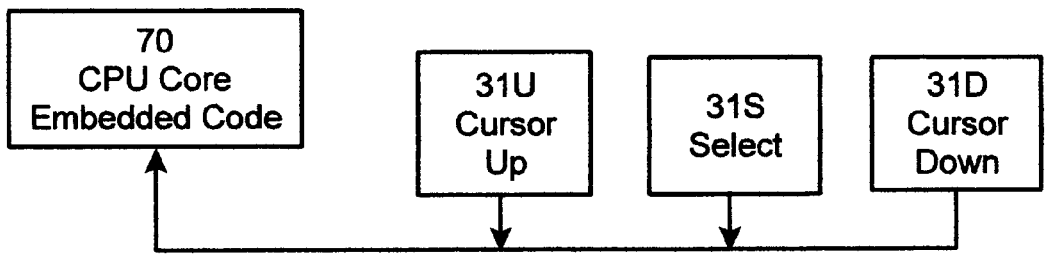
FIG. 18 is a push button array shown as block diagrams of circuits for that function and operation.

Referring to block diagram FIG. 17, power circuits includes a 3.6V battery pack 66 to provide up to 32 hours of mobile operating power to the portable personal safety indicator 25. All critical circuitry of portable personal safety indicator 25 including CPU core 70 is capable of running at operating voltages as low as 2.0 volts. Since 3.6V battery pack 66 is not allowed to discharge below 2.6 Volts, this leaves ample headroom for reliable portable personal safety indicator 25 operations. CPU core 70 periodically monitors the current voltage output of 3.6V battery pack 66 and notifies the user when it is time to recharge the battery pack 66 or switch to an external power source 64. External power source 64 contains logic circuitry to recharge within 1.2 hours 3.6 V battery pack 66. In addition portable personal safety indicator 25 contains a self-resetable fuse circuit which helps protect portable personal safety indicator 25 and external power source 64 from potential damage due to possible short circuits or overload conditions. On/Off Switch 32 shown in FIG. 17 enables power to portable personal safety indicator 25 in addition to another self-resetable fuse circuit which helps protect the portable personal safety indicator 25, any connected external power source 64 and 3.6 V battery pack 66 from potential damage due to possible short circuits or circuit overload conditions. On/Off Switch 32 provides power from 3.6V battery pack 66 to −3.6V inverter 67 and battery to 5V converter 68. A battery to 5V converter 68 converts the battery pack 66 voltage into a stable 5 volt supply for various circuits. The −3.6V inverter converts the positive battery pack 66 voltage into an equivalent negative value for use in analog circuits. The output of battery to 5V converter 68 is used by a 5V to 10V converter 69 to generate a stable 10V voltage reference for radiation sensor 120, see FIG. 13. A 10V to 5V ref generator 62 converts the output of 5V to 10V converter 69 to a stable 5 volt reference voltage for use by various circuits. The preceding reference voltages are generated in the manner known to skilled artisans to insure that circuit noise is not coupled into sensitive measurement circuits. The characteristics of power circuit 80 as previously described includes external power source 64 for portable personal safety indicator 25 with a typical life expectancy of three years before 3.6V battery pack 66 would require replacing. In FIG. 18 there is a push button array 31 consisting of three momentary contact switches, cursor up 31U, select present function 31S, and cursor down 31D which are used to navigate the main menu 88 and initiate specific functions as detailed in FIG. 19, push button main menu 88 structure. Portable personal safety indicator 25 is powered up into the run mode continuously monitoring according to factory default settings or user specified settings. Push button array 31 provides an active low interrupt signal to CPU core 70 when any switch is depressed. All user input to the portable personal safety indicator 25 is via push button array 31. Operational commands to the portable personal safety indicator 25 can also be initiated by validated control commands through the infra red data interface 160 or the PCS RF link 131 which is a subsection of EMF detector 130. Main menu 88 functions are accessed by the user depressing push button 31S for two or more seconds. LCD display 26 will indicate that the portable personal safety indicator 25 is in main menu 88 mode by displaying "-Main Menu" followed by the sequential display of available main menu 88 selections consisting of "audio player, calibration, constant monitor mode, digital recorder, operation settings, infra red data interface, PCS RF link 131 Voice Messages and run." Main menu 88 functions not specifically described are well known and skill artisans would understand how those are included in the portable personal safety indicator 25. Available main menu 88 functions are continuously displayed for two seconds each in a round robin fashion until the user selects the current displayed function by depressing push button 31S or by depressing push button 31U to go back up one selection in main menu 88 or by depressing push button 31D to go down one selection in main menu 88. Once any of the switches 31S, 31U or 31D is depressed the round robin displaying of main menu 88 functions ceases until 30 seconds has elapsed without any further user input. The portable personal safety indicator 25 defaults back to the run mode if no user input is provided after one minute. Selection of "Audio Player" branches to the submenu consisting of "Erase Selection, Play Selection and Volume Up/Down." Digital recorder functions include choosing play selections, erasing previously recorded audio and recording new audio sessions. Microphone 68 sensitivity and speaker 28 volume can also be adjusted through this main menu 88.

Figure 19:
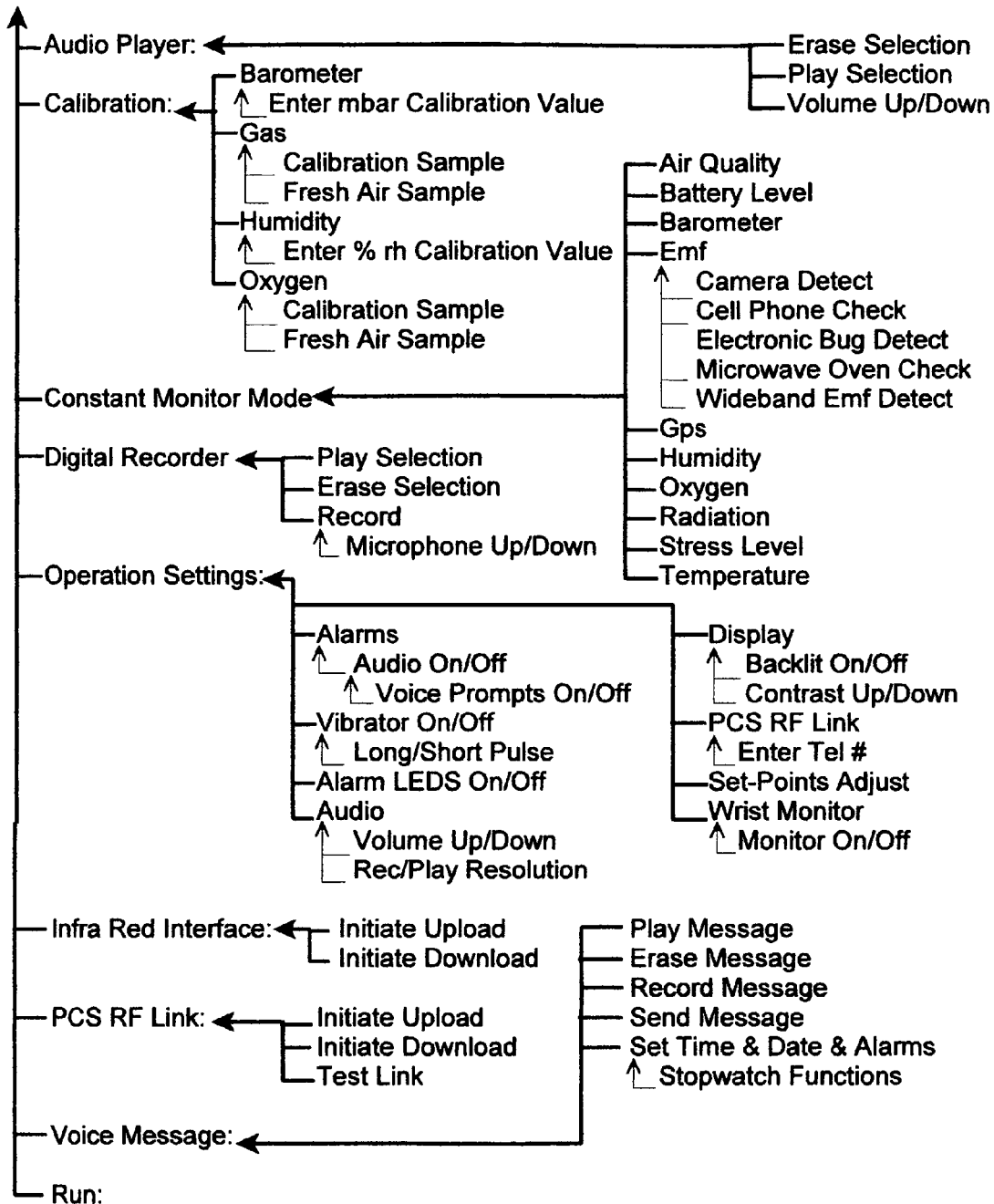
FIG. 19 is a push button user menu structure shown for the main menu selection for aiding understanding of its function and operation.

Operation is simple as available main menu 88 functions are continuously displayed for two seconds each in a round robin fashion until the user selects the current displayed function by depressing push button 31S or by parsing up or down the main menu 88 tree by depressing push button 31U or push button 31D until the desired selection is displayed and depressing push button 31S to initiate the current displayed selection. Again the portable personal safety indicator 25 defaults back to the run mode if no user input is provided after one minute. Normally, the user will select "Play Selection" when in the "Audio Player" sub-menu, which in turn displays a list of available selections to play. The user picks a selection using concepts previously described. Play selections are downloaded to the portable personal safety indicator 25 using the infra red data interface 160 or the PCS RF link 131. Other available functions listed in FIG. 19 are also accessed with concepts previously described. Again depressing push button 31U causes the portable personal safety indicator 25 to go back one layer in main menu 88. A "Calibration" sub-menu of main menu 88 allows for field recalibration of the barometer, gas, humidity and oxygen sensors. Sub-menu, Constant monitor mode herein "CMM" is a special operational method which allows for continuous monitoring of selected functions, i.e., sources of air contaminants can be measured and located using CMM and selecting air quality to detect where in an environment the strongest concentration of air borne contaminants are located. In this manner, the portable personal safety indicator 25 acts as a hunt-and-seek-detector. CMM battery level runs a special load test on power circuit 80 to determine if a battery pack 66 may need replacing. CMM barometer can be used to detect pressure changes which are helpful in locating facility leaks and as an intrusion detection alarm i.e., sudden changes in pressure can be an indicator that a door or window has been opened or closed. CMM EMF detection can be used to detect and locate cameras, perform cell phone transmission power safety checks, detect and locate electronic bugs, check microwave oven safety by checking for leaks or excessive external transmissions and do wideband EMF source generation determination. CMM GPS displays current GPS coordinates in real time which is useful for real time navigation or -location determination applications. CMM humidity sensing can be used to calibrate environmental HVAC humidity control systems or detect damp areas which may indicate plumbing or structural leaks. CMM oxygen measuring can be used to calibrate medical equipment i.e., oxygen generators, oxygen concentrators, in addition to real time monitoring of closed space areas and inhabited environments to address potential safety concerns and verify adequate ventilation. CMM radiation detection can be used to locate radiation sources. CMM temperature measurement is useful for detecting air leaks, locating thermal generation sources and calibrating HVAC thermostats. CMM stress level results are useful for determining overall environmental safety taking into account all portable personal safety indicator 25 measurements. The sub-menu, "operation settings" of main menu 88 section allows the user to adjust the operating parameters of the portable personal safety indicator 25 including alarm conditions such as turning the audio on/off, selecting voice prompts (defaults to alarm tones if audio is on and voice prompt is off), turning vibrator 150 on/off (if on then pulse duration of vibrator 150 can be set to long or short pulse duration), turning alarm LEDS 30 on/off (certain military, police or covert applications would typically have audio off, vibrator 150 on and alarm LEDS 30 off). Audio menu selection allows the user to turn the speaker 28 volume up/down. Using the display main menu 88 selection, the user can turn the backlit on/off and adjust the contrast up/down. PCS RF link 131 menu selections allow the user to enter or change a telephone number which is used by PCS RF link 131 to call for remote uploading, reporting or downloading of data. The wrist monitor menu selection is used to enable or disable wrist monitoring functions. Infra red data interface 160 menu section provides for initiating uploads or downloads via infra red data interface 160. Typical applications include uploading historical measurement data to a PC for reporting functions, exchanging data with another portable personal safety indicator 25 and downloading CPU core 70 embedded code updates or play selections to be stored in nonvolatile memory of CPU core 70. PCS RF link 131 menu section provides for initiating uploads or downloads via PCS RF link 131. Typical applications include field reporting of real time measurement data and command control functions for first responders, military, police and commercial applications. Uploads and downloads can also be remotely initiated by the portable personal safety indicator 25 remote command control software. In addition the PCS RF link 131 may be tested using the "Test Link" sub-menu selection which executes a software subroutine that dials the Telephone number previously entered for PCS RF Link functions and tests for proper communications capability.

Referring to block diagram FIG. 20, infra red data interface 160 has an infra red transmitter 133 and an infra red receiver 134 to form a full duplex infra red data interface 160 capable of data rates up to 250k baud. Infra red data interface 160 provides for uploading or downloading historical measurement data to a PC for reporting functions, exchanging data with another portable personal safety indicator 25 and downloading CPU core 70 embedded code updates or play selections to be stored in nonvolatile memory of CPU core 70. A website can be maintained for downloading play selections to a user PC on a cost per download basis for subsequent download to the portable personal safety indicator 25. Infra red receiver 134 incorporates a comparator circuit with significant noise immunity to protect against spurious receive signals. In addition, all communications through infra red data interface 160 uses a start ID pattern and end of data packet CRC to insure that only valid data packets are received. Each portable personal safety indicator 25 has a unique embedded serial number which is used to generate a unique start ID pattern. Received start ID patterns which do not match the portable personal safety indicator's 25 embedded serial number are ignored, however the portable personal safety indicator 25 does use the reception of other valid start ID patterns to adjust its transmit/receive timing to avoid data collisions from any one or more other portable personal safety indicator 25.

With portable personal safety indicator 25 by using remote command control software and an external large area infra red transmitter, infra red data interface 160 may be used to receive remote global commands. This is useful for factory calibration operations where several portable personal safety indicator 25 (up to several hundred) are put into a specific environment at the same time (i.e., a specific gas environment, humidity, etc) and remotely instructed to enter various calibration modes and save their respective individual measurements into non volatile memory of CPU core 70. Another application of this feature includes wide area broadcast of command control functions to multiple field personnel (military, swat team, etc.).

Figure 21:
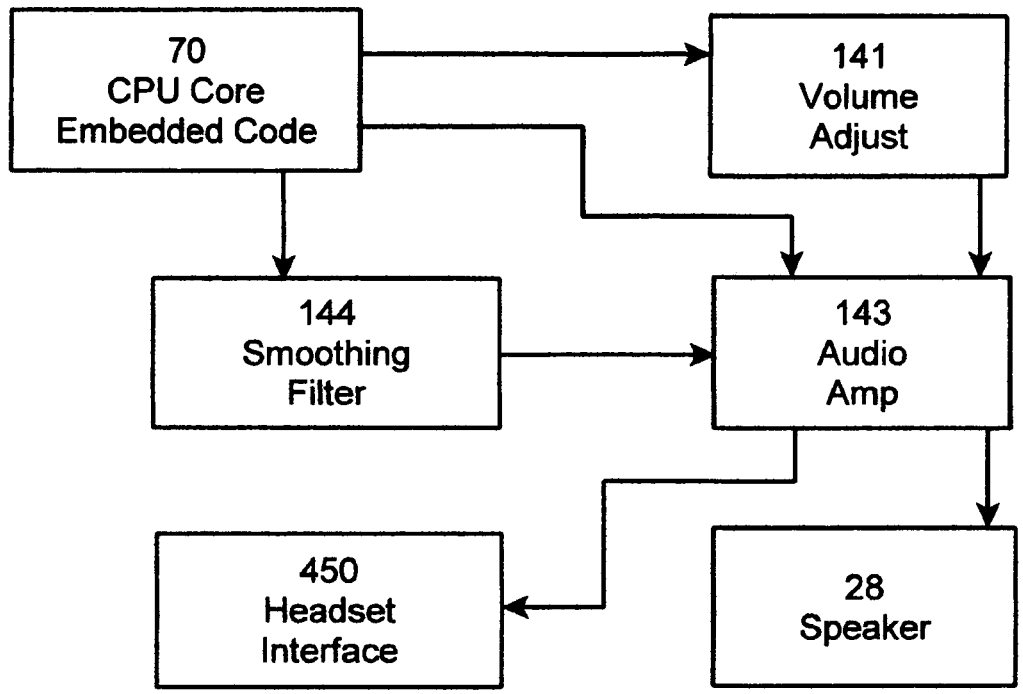
FIG. 21 is an audio circuit shown as block diagrams of circuits for that function and operation.

Referring to block diagram FIG. 21, audio circuits 140. CPU core 70 uses volume adjust 141 to digitally adjust the volume of audio circuits 140. Volume adjust 141 controls the gain of audio amplifier 143 that receives analog signals for amplification from CPU core 70 or a smoothing filter. CPU core 70 outputs high quality digital audio directly to audio amplifier 143 using 8, 10 or 12 bit D/A conversion at rates up to 44 K samples per second. D/A conversions are used for audio player and digital recorder functions in FIG. 21 and associated disclosure herein. CPU core 70 also has digital PWM herein "pulse width modulation" and square wave output to generate audio output. PWM and square wave signals are received from CPU core 70 and processed by smoothing filter 144 to generate a pleasing bandwidth audio signal without significant harmonic distortion. Audio amplifier 143 receives and amplifies the processed PWM and square wave signal from smoothing filter 144. PWM and square wave modes require considerably less data storage than D/A digital audio output. Speaker 28 receives the amplified signal from audio amplifier 143. If an external headset 61 is plugged into headset interface 450, speaker 28 is automatically disconnected from audio amplifier 143. Audio circuit 140 is capable of reproducing audio from 120 Hz to 20 KHz with a sound pressure of 81 db and one watt RMS with a total harmonic distortion "THD" of 0.75%.

Figure 22:
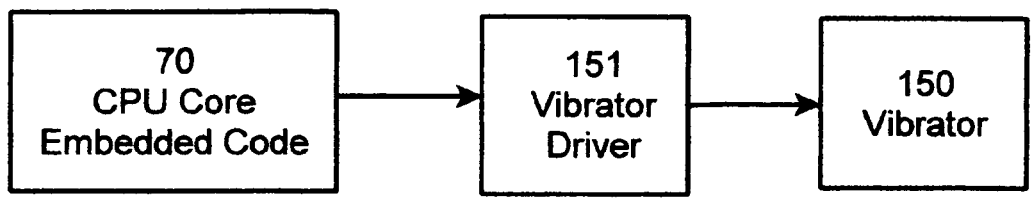
FIG. 22 is an alarm vibrator shown as block diagrams of circuits for that function and operation.

Referring to block diagram FIG. 22, vibrator 150 has a driver 151 for providing power thereto as determined by CPU core 70. Through main menu 88 functions of the portable personal safety indicator 25 vibrator 150 can be enabled or disabled. When enabled, the vibrator 150 pulse mode can be set to a long pulse or several short pulses which will repeat on a 30 second interval for two minutes. If no response is received from the user, pulsing will discontinue and LCD Display 26 will indicate an unacknowledged alarm status. Vibrator 150 is generally used for manners mode, hearing impaired and covert applications. Vibrator 150 is capable of a rotational velocity of 13,000 rpm with minimum deflection strength of 9.8 N.

Figure 23:
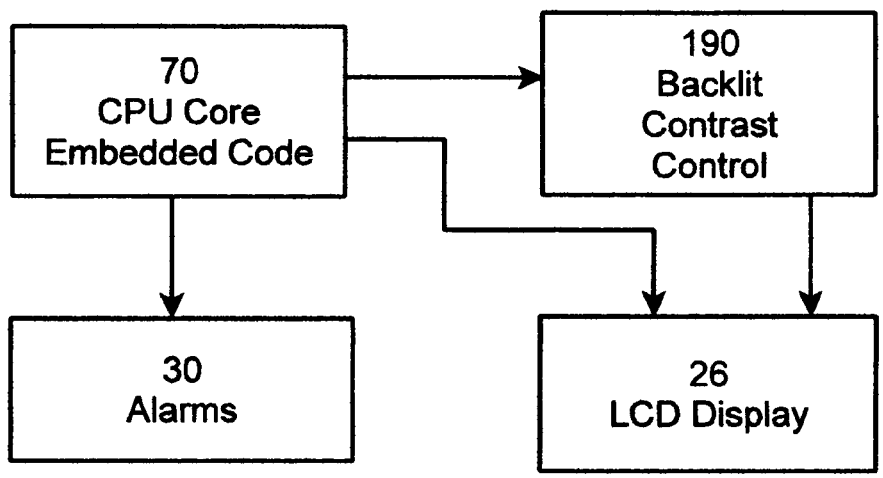
FIG. 23 is a LCD display and alarm LEDS signal shown as block diagrams of circuits for that function and operation.

Referring to block diagram FIG. 23, with LCD display 26 alarm LEDS 30 wherein all measurement data and user text prompts are displayed on LCD display 26 which is an alphanumeric LCD display 26 consisting of two lines of eight characters each. Text prompts exceeding eight characters in length are horizontally scrolled every five seconds. Each displayable character of LCD display 26 consists of a programmable 5×7 font format which is programmed by CPU core 70 to support multiple user languages. All information displayed on LCD display 26 is written to an embedded memory of LCD display 26 by CPU core 70. Backlit contrast control 190 controls the contrast and backlighting of LCD display 26 according to instructions from CPU core 70. Alarm LEDS 30 is used to turn on or flash LED 30 alarm of any portable personal safety indicator 25 according to current environment measurements and associated alarm set point settings. Using alarm LEDS 30, CPU core 70 controls the status of all alarm LEDS 30 i.e., on, off or flashing. LEDS 30 provide eight alarms, one each for air quality, oxygen, temperature, humidity, radioactivity, EMF, stress level and battery level.

Figure 24:
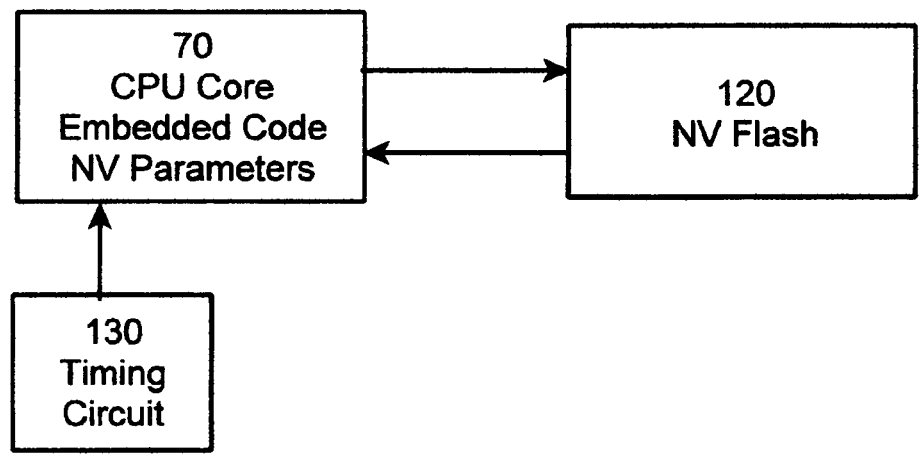
FIG. 24 is a CPU core shown as block diagrams of circuits for that function and operation.

Referring to block diagram FIG. 24 CPU core 70, block 100 as a single component micro-controller containing all embedded code in internal flash memory needed to execute portable personal safety indicator 25 functions. The embedded code is secured using a programmed security bit that prohibits the embedded code from being read out externally. The single component micro-controller "SCM" also contains NV Ram "non volatile memory" for storage of operating parameters, calibration values and lookup tables used by embedded code. The SCM also contains NV Ram "read, write memory" which is used during embedded code program execution. An external NV flash 120 is used to store up to three months of portable personal safety indicator 25 measurements, digital recordings and downloaded play selections. Up to several hours of digital audio can be stored in NV flash 120 subject only to the sample rate and bit resolution used and size in megabytes of NV flash 120. Timing Circuit 130 provides all system clock sources from which CPU core 70 generates all other necessary timing signals for system operation.

In addition to the mentioned applications of the portable personal safety indicator 25, skilled artisans will appreciate that it can be monitor the environment for conditions that may be detrimental to an individual's health. Although the disclosure herein has been set forth with reference to particular embodiments, it is to be understood that those are merely illustrative of the principles and applications of any portable personal safety indicator. It is therefore to be understood that numerous modifications may be made to the illustrative embodiments and that other arrangements may be devised without departing from the spirit and scope of the apparatus and method here after claimed. Variations in the physical characteristics of portable personal safety indicator including methods of use, construction, material used or nomenclature should be considered as evident alternatives to the current description or implementation of portable personal safety indicators.

What is claimed is:

1. A system for intelligently monitoring, detecting and evaluating hazardous situations around and within a person, the system with two way communications comprising:
   a plurality of portable personal safety indicator for carrying on the person, each portable personal safety indicator receiving and monitoring inputs for determining environmental status in real time about the person and transmitting and receiving signals;

a single component micro-controller in each portable personal safety indicator containing an embedded code in internal flash memory for execution of functions and non volatile memory for storing operating parameters, calibration values and lookup tables for use by embedded code for transmitting for decision making in each portable personal safety indicator;

a signaling system within each portable personal safety indicator single component micro-controller for communication with each portable personal safety indicator, the signaling system single component micro-controller capable of monitoring, recording and reporting information received from each portable personal safety indicator inputs;

a sensor unit in each portable personal safety indicator including a plurality of sensors communicating with the signaling system to provide multiple and frequent environmental status updates in real time;

a radio signal positioning system in communication with each portable personal safety indicator, and for processing information related to identification of environmental hazardous situations and providing preferred escape or safety instructions to each portable personal safety indicator in real time.

2. The system of claim 1 wherein a portable power circuit is in each portable personal safety indicator to operate the signaling system.

3. The system of claim 1 wherein the plurality of sensors includes sensors for conditions of humidity, temperature, gases, radioactivity, EMF radiation, and other hazards not readily available to human senses so that the embedded code can apply one or more of the sensed conditions via the lookup tables to normalize the monitoring of the hazards.

4. Amended The system of claim 1 wherein each portable personal safety indicator includes a camera for monitoring the vicinity proximate the portable personal safety indicator, the camera includes a visible and an invisible radiation sensitive monitor.

5. The system of claim 1 wherein each portable personal safety indicator includes a microphone for monitoring, recording ambient sound and for voice communicating audio information proximate each portable personal safety indicator.

6. The system of claim 1 wherein each portable personal safety indicator includes a speaker to project audio warnings and instructions in the vicinity proximate the sensor unit.

7. The system of claim 1 wherein each portable personal safety indicator includes a display screen to provide visual information in the vicinity proximate the sensor unit.

8. The system of claim 2 wherein each portable personal safety indicator includes standardized connections for connection to an external power source and communications circuits, for recharging the portable power circuit and for linking to the a central station or an external computer.

9. The system of claim 1 wherein each portable personal safety indicator single component micro-controller stores monitored sensor data and significant changes are frequently input to a memory therein for recording the history of environmental hazards.

10. The system of claim 9 wherein one of the plurality of the sensors receives signals from earth orbiting satellites in a Global Positioning System for determining the location of the portable safety indicator.

11. The system of claim 1 wherein two way communications with each portable personal safety indicator are provided with other portable personal safety indicators, a central station or an external computer by one or more of the following communications: RF, analog, digital or light-wave technologies.

12. The system of claim 11 wherein the communication is PCS RF link wireless remote communications via PCS cell phone technology for selectively receiving and transmitting between each portable personal safety indicator and any other, central station or the external computer.

13. The system of claim 12 wherein the selective receiving and transmitting is associated with specific radio identification by a unique embedded serial number for each portable personal safety indicator.

14. The system of claim 11 further comprising in each portable personal safety indicator single component micro-controller an information processing system for receiving and transmitting to each, some or all portable personal safety indicators and for processing information from each, some or all of the plurality of sensor units, the central station or the external computer.

15. The system of claim 14 wherein each information processing system provides frequently updated real time data from the single component micro-controller with hardware and permanent and programmable software.

16. The system of claim 14 wherein the information processing system has and operates through system algorithms to normalize the sensor inputs.

17. The system of claim 16 wherein the system algorithms include logic and allow calculations.

18. The system of claim 14 wherein communication between each portable personal safety indicators and the central station information processing system or the external computer are accomplished via radio signals amongst the portable personal safety indicators or with the central station information processing system or the external computer.

19. The system of claim 14 wherein each portable personal safety indicator information processing system is in communication with telephone including "911" and emergency responders.

20. The system of claim 19 includes redundant geographically dispersed backup arrangements.

21. The system of claim 20 wherein the geographically dispersed back-up arrangements include any cell phone or satellite communications link.

22. The system of claim 20 wherein the one or more satellite located central stations are solar or battery powered and each functions totally independently of any other back-up arrangements.

23. The system of claim 20 wherein the personal portable safety indicators are networked to each other and on a frequent and periodic basis for updates inputs of each personal portable safety indicator in real time.

24. A portable personal safety indicator for monitoring, detecting, evaluating and recording hazardous situations about and within a person comprising:

a device compact for carrying on the person, the device receiving inputs for monitoring conditions about and within the person and generating signals relative thereof in real time;

a portable power circuit within the device for energizing the device;

a signaling system within the device for warning at least the person, the signaling system including electronic, physical, audible or visual output for the person;

one or more sensors responsive to at least one or more of the ambient conditions about and vital signs or physiological conditions of the person, the one or more sensors sensitive to at least levels of hazardous gases, ionizing radiation levels, electro magnetic radiation including RF and microwave transmissions, unsafe temperature, humidity and air pressure, and a single component micro-controller in the device energized by the portable power circuit, the single component micro-controller positioned for receiving information from the one or more sensors, the single component micro-controller capable of communicating, monitoring, recording and reporting information received from the one or more sensors as inputs, the single component micro-controller for making decisions connected to the signaling system for providing real time output on ambient and physiological conditions about and within the person including changes thereof indicative of hazardous conditions.

25. The portable personal safety indicator of claim 24 wherein the one or more sensors in the device are arranged to provide multiple and frequent ambient and physiological status updates as to at least the person carrying the portable personal safety indicator the output from the signaling system.

26. The portable personal safety indicator of claim 25 wherein the one or more sensors check levels of hazardous conditions not readily recognized by the senses of the person including air pollutants, smoke and exhaust fumes, low oxygen levels, adverse radiation levels and ambient conditions of unsafe temperature, humidity and air pressure against acceptable ranges set in a memory within the single component micro-controller and issue warning to the person.

27. The portable personal safety indicator of claim 26 wherein an oxygen sensor monitors constantly ambient oxygen levels and oxygen level measurements are made by single component micro-controller core as A/D conversions of the measured current analog voltage value received from oxygen sensor.

28. The portable personal safety indicator of claim 25 wherein the one or more sensors is located adjacent the person on a wrist band to check vital signs for hazardous conditions not readily recognized by the senses of the person including blood pressure, heart rate, blood oxygen and temperature unsafe against acceptable ranges set within the single component micro-controller and transmit a warning or communicate changing vital signs that are monitored.

29. The portable personal safety indicator of claim 25 wherein a microphone monitors audio information proximate the sensor unit.

30. The portable personal safety indicator of claim 25 wherein a speaker projects audio warnings in the vicinity proximate the portable personal safety indicator for warning the person of hazards and dangers.

31. The portable personal safety indicator of claim 30 wherein a display screen is provided to provide visual information accessible to the person.

32. The portable personal safety indicator of claim 25 wherein the portable power circuit is rechargeable via connection to an external power source.

33. The portable personal safety indicator of claim 25 wherein a timed input to a memory therein for recording the history of ambient and physiological conditions based on the single component micro-controller embedded algorithms and software analysis and decisions.

34. The portable personal safety indicator of claim 24 wherein the one of sensors receives signals from earth orbiting satellites in a Global Positioning System.

35. The portable personal safety indicator of claim 25 wherein two way communications with the device are provided with one or more of the following communications analog, digital, RF or light-wave technologies.

36. The portable personal safety indicator of claim 24 comprising a central station or an external computer information processing system for receiving and transmitting to each, some or all devices and for processing information from each.

37. The portable personal safety indicator of claim 36 wherein PCS RF link provides wireless remote communications via PCS cell phone technology for receiving and transmitting and includes specific identifications for each device.

38. The portable personal safety indicator of claim 36 wherein the communications are for selectively receiving and transmitting between each device and any other or the central station or the external computer.

39. The portable personal safety indicator of claim 36 wherein the portable personal safety indicator, the central station or the external computer information processing system includes the single component micro-controller with hardware and permanent and programmable software.

40. The portable personal safety indicator of claim 36 wherein the portable personal safety indicator, the central station or the external computer information processing system have and operates through system algorithms.

41. The portable personal safety indicator of claim 40 wherein the system algorithms include logic and allow calculations.

42. The portable personal safety indicator of claim 38 wherein the portable personal safety indicator the single component micro-controller includes normalization lookup tables for the input measurements from each of the sensors for, barometric pressure, temperature, humidity, oxygen, RF RMS, gas associated characteristic individual response curves to identify air borne contaminants, the lookup tables data determine in real time and perform threat assessment of current environmental conditions.

43. The portable personal safety indicator of claim 38 wherein the single component micro-controller contains non volatile memory for storage of operating parameters, calibration values and lookup tables used by embedded code, and the single component micro-controller contains read, write memory is used during embedded code program execution.

44. The portable personal safety indicator of claim 31 the speaker, display screen or both are capability for providing, information, news or entertainment there through.

45. The portable personal safety indicator of claim 24 wherein the single component micro-controller has a core that includes non-volatile memory.

46. The portable personal safety indicator of claim 24 wherein the portable power circuit includes a rechargeable battery, capacitor, manually activated generator or solar for having maximum portability.

47. The portable personal safety indicator of claim 30 wherein a menu for selectively operating the portable personal safety indicator is included in the display screen.

48. A method for operating a portable personal safety indicator for monitoring, detecting, evaluating and recording hazardous situations about and within a person in real time, the method having the steps of:

having the portable personal safety indicator near the person;

receiving inputs via one or more sensors for monitoring conditions about and within the person and generating signals relative thereof;

energizing the indicator with a portable power circuit;

warning at least the person with an alarm system;
receiving information as inputs from the one or more sensors connected to a single component micro-controller including stored parameters and embedded algorithms capable of monitoring, recording and reporting information by making decisions in real time, and
providing output from a the single component micro-controller on changing ambient and physiological conditions about and within the person including changes thereof indicative of hazardous ambient conditions and changing vital signs in real time from the single component micro-controller to any and all other portable personal safety indicators, a central station or an external computer.

49. The method of claim 48 with the step of having multiple and frequent ambient and physiological status updates as the output from the portable personal safety indicator alarm system.

50. The method of claim 48 with the step of checking hazardous conditions not readily recognized by the persons senses including air pollutants, smoke and exhaust fumes, low oxygen levels, adverse radiation levels and ambient conditions of unsafe temperature, humidity and air pressure against acceptable ranges set within the single component micro-controller and for comparing the checked results against monitored vital signs of the person.

51. The method of claim 50 with the step of monitoring physiological conditions not readily recognized by the senses of the person including one or more sensors on a wrist band blood pressure, heart rate, blood oxygen and temperature unsafe against acceptable ranges set within the single component micro-controller.

52. The method of claim 48 with the step of supplying as determined by the step of monitoring hazard and physiological information to the person by vibration, visually or by audio signals.

53. The method of claim 48 with the step of projecting audible warning with a speaker in the vicinity proximate the portable personal safety indicator.

54. The method of claim 48 with the step of showing with a display screen and LEDs visual information accessible to the person.

55. The method of claim 48 with the step of including rechargeable batteries in the portable power circuit that can be recharged by connection to an external power source.

56. The method of claim 48 with the step of receiving periodically from the single component micro-controller monitored and determined dangers or hazards to a memory therein for recording the history of ambient and physiological conditions.

57. The method of claim 48 with the step of having a PCS RF link for wireless remote communications via PCS cell phone technology for receiving and transmitting and includes specific identifications for each portable personal safety indicator.

58. The method of claim 48 with the step of selectively receiving and transmitting between each portable personal safety indicator single component micro-controller and any other portable personal safety single component micro-controller or a central station or the external computer.

59. The method of claim 48 with the step of using of stored parameters and embedded algorithms based on the knowledge and resources of experienced technical person in fields relating to emergency situations including fire fighting, toxic fume detection, earthquake physics, human tolerance to radiation, gases, temperature and medical problems detectable from changes in surrounding conditions and/or monitored bodily physiology to aid in protecting the person.

60. The method of claim 48 with the step of monitoring and determining with embedded algorithms continuously environment exposures including hazardous gases, elevated levels of other air pollutants including smoke and exhaust fumes, low oxygen levels, ionizing radiation levels, adverse radiation levels of Electro Magnetic Radiation "EMF", radiation including RF and microwave transmissions, unsafe temperature, humidity and air pressure.

61. The method of claim 60 with the step of maintaining a three months user history of all exposure levels and duration for uploading to a PC via infrared data interface and for reporting functions.

62. The method of claim 48 with the steps of analyzing and comparing to stored contaminant profiles in normalization lookup tables to determine what family classification of contaminant is present when assessing a threat to the environment.

63. The method of claim 48 with the steps of monitoring, detecting and alerting of environmental radiation sources by auto-scaling used to get the instantaneous radiation exposure level and exposure duration data for storage and later readout for auto scaling radiation detection and dosage with excellent measurement bandwidth.

64. The method of claim 48 with the steps of providing EMF detection and metering EMF dosage by scanning continuously for EMF, in the frequency range of approximately 100 khz to 20 ghz at levels of 1 nano watt to 10 watts RMS/cm$^2$ with an accuracy of +/−10% and auto scaling with circuitry to accurately detect RMS EMF radiation levels and exposure durations for storage and subsequent readout.

65. The method of claim 49 with the steps of measuring ambient temperature, humidity and barometric pressure and monitoring EMF for spikes over time and using software for predicting hazardous weather changes as an indicator of danger to the person.

66. The method of claim 65 with the steps of providing accurate gas sensor self-calibration by using ambient data of oxygen, temperature, humidity and pressure for normalizing gas sensor with real-time measurement of environmental variables readings.

67. The method of claim 48 with the steps of monitoring automatically the environment for dangerous air borne gases and other air pollutants, detecting, classifying up to several hundred different toxic gases, and notifying the user of environmental problems.

68. The method of claim 67 with the steps of monitoring continuously the environment for ambient oxygen levels, radiation sources for indicating radiation detection and radiation dosage, scanning continuously for electro magnetic radiation, EMF radiation and EMF Dosimeter, electronic bugs including RF transmitters, microphones and cameras.

69. The method of claim 48 with the step of having the portable personal safety indicator near the person includes wearing by the person externally or in a carrier leaving plugged into an AC wall outlet or attaching to a vehicle dash or by hand held use.

70. The method of claim 66 with the step of using electrochemical cells as gas sensors sensitive to environmental variations including temperature, humidity, barometric pressure and ambient oxygen levels.

71. An auto-scaling detector dosimeter comprising,
a sensor for monitoring radiation in an environment, the sensor producing signals indicative of the radiation sensed over time;

a variable gain amplifier first stage integrator connected to receive signals indicative of the radiation sensed over time from the sensor, the variable gain amplifier including a CPM counter clock having frequency and comparator reference voltage;

an integrated pulse comparator coupled to the variable gain amplifier first stage integrator;

an adjustment circuit for reading pulses from the integration pulse comparator and determining when pulses indicative of the radiation sensed over time reach maximum length for the current gain setting of variable gain first stage integrator amplifier, the adjustment circuit coupled to control the variable gain amplifier first stage integrator by repeatedly decreasing the gain and adjusting the CPM counter clock frequency and comparator reference voltage to prevent topping out of the variable gain amplifier first stage so the receive pulse signals indicative of the radiation sensed over time are within current scale settings, the adjustment circuit thus automatically making order of magnitude adjustments that force the range of the variable gain amplifier first stage integrator to hover centrally about its current gain/output setting.

72. The auto-scaling detector dosimeter of claim 71 wherein adjustment circuit readjusts the variable gain amplifier first stage integrator, CPM counter clock frequency and comparator reference voltage to a decaying or increasing signals indicative of the radiation sensed over time prior to establishment of a new scaling factor.

73. The auto-scaling detector dosimeter of claim 71 wherein the adjustment circuit includes an auto-scaling algorithm for monitoring signals indicative of the radiation sensed over time, the auto-scaling algorithm adjusts the analog gain of the variable gain amplifier first stage integrator, CPM counter clock frequency and comparator reference voltage preventing a continuous high or low pulse from the integration pulse comparator based on a moving average of the signals indicative of the radiation sensed over time.

74. The auto-scaling detector dosimeter of claim 71 wherein the sensor includes a pin photodiode with a large surface area for a depletion region created by reverse biasing the pin photodiode so collisions of radioactive particles produce an associated charge increase therein proportion to the energy imparted from the particle.

75. An auto-scaling detector dosimeter comprising, a sensor for monitoring EMF in an environment, the sensor producing signals indicative of the EMF sensed over time;

a difference amplifier connected to receive signals indicative of the EMF sensed over time from the sensor, the difference amplifier responsive to receive signals versus a current gain setting and to produce an output indicative of the gain;

an adjustment circuit for reading the output of the difference amplifier and determining when the EMF sensed over time reach maximum analog voltage for the current gain setting, the adjustment circuit coupled to control the difference amplifier by repeatedly decreasing the gain and adjusting the difference amplifier voltage to prevent topping out of the difference amplifier so the receive signals indicative of the EMF sensed over time are within current scale settings, the adjustment circuit thus automatically making order of magnitude adjustments that force the range of the difference amplifier to hover centrally about its current gain/output setting.

76. The auto-scaling detector dosimeter of claim 75 wherein the sensor includes an array of tuned micro-strip antennas coupled to a wideband RF amplifier and the difference amplifier output for the signals indicative of the radiation sensed over time from the EMF detector.

* * * * *